US011996183B2

(12) United States Patent
Rowe et al.

(10) Patent No.: US 11,996,183 B2
(45) Date of Patent: May 28, 2024

(54) METHODS OF ANALYZING DIAGNOSTIC TEST KITS

(71) Applicant: Scanwell Health, Inc., Los Angeles, CA (US)

(72) Inventors: Aaron Alexander Rowe, Toluca Lake, CA (US); Hui-Ling Koh, Santa Ana, CA (US); Stephen L. Chen, Tustin, CA (US); Yunyuan Vivian Wang, Tustin, CA (US)

(73) Assignee: Scanwell Health, Inc., Los Angeles, CA (US)

( * ) Notice: Subject to any disclaimer, the term of this patent is extended or adjusted under 35 U.S.C. 154(b) by 0 days.

(21) Appl. No.: 17/222,819

(22) Filed: Apr. 5, 2021

(65) Prior Publication Data

US 2022/0084659 A1 Mar. 17, 2022

Related U.S. Application Data

(60) Provisional application No. 63/079,975, filed on Sep. 17, 2020.

(51) Int. Cl.
*G16H 30/00* (2018.01)
*G01N 33/487* (2006.01)
(Continued)

(52) U.S. Cl.
CPC ........ *G16H 30/40* (2018.01); *G01N 33/48785* (2013.01); *G01N 33/5302* (2013.01); *G01N 33/54388* (2021.08); *G01N 2458/00* (2013.01)

(58) Field of Classification Search
CPC ..................................................... G16H 30/40
(Continued)

(56) References Cited

U.S. PATENT DOCUMENTS

| 4,843,377 A | 6/1989 | Fuller et al. |
| 4,976,923 A | 12/1990 | Lipsky et al. |

(Continued)

FOREIGN PATENT DOCUMENTS

| CN | 206489079 U | 9/2017 |
| EP | 1963828 B1 | 9/2008 |

(Continued)

OTHER PUBLICATIONS

Blake et al., "Diagnosis of Porphyria—Recommended methods for peripheral laboratories". The clinical biochemist—Reviews. May 31, 1992 (May 31, 1992). pp. 1-13. XP055768951, Retrieved from the Internet: URL:https://www.aacb.asn.au/documents/item/150 [retrieved on Jan. 26, 2021] Method; p. S7.

(Continued)

*Primary Examiner* — Elizabeth A Robinson
*Assistant Examiner* — Emily R. Berkeley
(74) *Attorney, Agent, or Firm* — Knobbe, Martens, Olson & Bear LLP

(57) ABSTRACT

A method for analyzing a diagnostic test may include receiving an image depicting a diagnostic test, wherein the diagnostic test comprises a test region indicating a test result, validating quality of the image, locating a test region image portion of the image depicting the test region of the diagnostic test; and predicting the test result based on the test region image portion. Furthermore, a method for facilitating analysis of a diagnostic test may include receiving one or more images depicting one or more control markings on a scan surface, wherein the one or more control markings are representative of one or more predetermined test results for the diagnostic test, and verifying detection of the one or more control markings in the one or more images using at least one computer vision technique.

22 Claims, 21 Drawing Sheets
(12 of 21 Drawing Sheet(s) Filed in Color)

(51) Int. Cl.
*G01N 33/53* (2006.01)
*G01N 33/543* (2006.01)
*G16H 30/40* (2018.01)

(58) Field of Classification Search
USPC .......................................................... 382/128
See application file for complete search history.

(56) References Cited

U.S. PATENT DOCUMENTS

| | | |
|---|---|---|
| 5,119,830 A | 6/1992 | Davis |
| 5,260,219 A | 11/1993 | Fritz |
| 5,408,535 A | 4/1995 | Howard, III et al. |
| 5,470,750 A | 11/1995 | Bar-Or |
| 5,501,837 A | 3/1996 | Sayles |
| 5,595,187 A | 1/1997 | Davis |
| 5,976,469 A | 11/1999 | Davis |
| D457,246 S | 5/2002 | Mazel et al. |
| 6,514,461 B1 | 2/2003 | Lappe et al. |
| 6,565,814 B1 | 5/2003 | Anraku et al. |
| 7,097,103 B2 | 8/2006 | Tseng |
| 7,190,818 B2 | 3/2007 | Ellis et al. |
| 7,197,169 B2 | 3/2007 | Wang |
| 7,267,799 B1 | 9/2007 | Borich et al. |
| 7,292,718 B2 | 11/2007 | Douglass |
| 7,313,257 B2 | 12/2007 | Roman |
| 7,344,081 B2 | 3/2008 | Tseng |
| 7,420,663 B2 | 9/2008 | Wang et al. |
| 7,428,325 B2 | 9/2008 | Douglass et al. |
| 7,474,390 B2 | 1/2009 | Robinson et al. |
| 7,622,729 B2 | 11/2009 | Duesbury |
| 7,652,268 B2 | 1/2010 | Patel |
| D633,209 S | 2/2011 | Boessneck et al. |
| D637,310 S | 5/2011 | Barbieux et al. |
| 8,068,666 B2 | 11/2011 | Gregory et al. |
| 8,073,248 B2 | 12/2011 | Brunner et al. |
| 8,145,431 B2 | 3/2012 | Kloepfer et al. |
| 8,150,115 B2 | 4/2012 | Capewell |
| 8,268,636 B2 | 9/2012 | Nazareth et al. |
| 8,506,901 B2 | 8/2013 | Chen et al. |
| D690,828 S | 10/2013 | Yoon et al. |
| 8,655,009 B2 | 2/2014 | Chen et al. |
| D712,060 S | 8/2014 | Tippett et al. |
| 8,809,066 B2 | 8/2014 | Matsumoto |
| 8,877,140 B2 | 11/2014 | Chen et al. |
| 8,889,424 B2 | 11/2014 | Ehrenkranz et al. |
| 8,911,679 B2 | 12/2014 | Chen et al. |
| 8,916,390 B2 | 12/2014 | Ozean et al. |
| 8,976,252 B2 | 3/2015 | Koh et al. |
| 8,998,613 B2 | 4/2015 | Jung et al. |
| 8,999,728 B2 | 4/2015 | Nazareth et al. |
| 9,042,630 B2 | 5/2015 | Binnig et al. |
| 9,063,091 B2 | 6/2015 | Tsai et al. |
| 9,230,187 B2 | 1/2016 | Hamsici et al. |
| 9,240,039 B2 | 1/2016 | Cong et al. |
| 9,285,323 B2 | 3/2016 | Burg et al. |
| 9,307,214 B1 | 4/2016 | Liu et al. |
| 9,354,181 B2 | 5/2016 | Barstis et al. |
| 9,386,221 B2 | 7/2016 | Kauniskangas et al. |
| 9,445,749 B2 | 9/2016 | Erickson et al. |
| 9,466,103 B2 | 10/2016 | Athelogou et al. |
| 9,466,104 B2 | 10/2016 | Tsai et al. |
| 9,489,703 B2 | 11/2016 | Kauniskangas et al. |
| 9,525,867 B2 | 12/2016 | Thomas et al. |
| 9,532,060 B2 | 12/2016 | Mesh-Iliescu et al. |
| 9,554,109 B2 | 1/2017 | Yao |
| 9,569,858 B2 | 2/2017 | Babcock et al. |
| 9,600,878 B2 | 3/2017 | Tsai et al. |
| 9,686,540 B2 | 6/2017 | Zhou et al. |
| 9,689,803 B1 | 6/2017 | Ruttner |
| 9,756,324 B1 | 9/2017 | Flanagan et al. |
| 9,778,200 B2 | 10/2017 | Tsai et al. |
| 9,787,815 B2 | 10/2017 | Erickson et al. |
| 9,818,193 B2 | 11/2017 | Smart |
| 9,824,441 B2 | 11/2017 | Satish et al. |
| 9,833,783 B1 | 12/2017 | Klein et al. |
| 9,857,372 B1 | 1/2018 | Pulitzer et al. |
| 9,857,373 B1 | 1/2018 | Pulitzer et al. |
| 9,863,811 B2 | 1/2018 | Burg et al. |
| 9,888,186 B2 | 2/2018 | Zhou et al. |
| 9,903,857 B2 | 2/2018 | Polwart et al. |
| 9,933,359 B2 | 4/2018 | Zehler et al. |
| 9,978,153 B2 | 5/2018 | Kisner et al. |
| 9,990,560 B2 | 6/2018 | Decker et al. |
| 10,019,656 B2 | 7/2018 | Huang et al. |
| 10,055,837 B2 | 8/2018 | Lee et al. |
| 10,068,329 B2 | 9/2018 | Adiri et al. |
| 10,088,411 B2 | 10/2018 | Shyam et al. |
| 10,089,753 B1 | 10/2018 | Fegyver et al. |
| 10,101,342 B2 | 10/2018 | Nazareth et al. |
| 10,132,802 B2 | 11/2018 | Ehrenkranz |
| 10,168,322 B2 | 1/2019 | Nazareth et al. |
| 10,175,162 B2 | 1/2019 | Jia et al. |
| 10,210,626 B2 | 2/2019 | Chiba et al. |
| 10,267,743 B2 | 4/2019 | Burg et al. |
| 10,331,924 B2 | 6/2019 | Pulitzer et al. |
| 10,352,946 B2 | 7/2019 | Nazareth et al. |
| 10,354,166 B2 | 7/2019 | Nahum et al. |
| 10,354,412 B2 | 7/2019 | Kisner et al. |
| D857,228 S | 8/2019 | Kaplan et al. |
| 10,395,368 B2 | 8/2019 | Berezhna et al. |
| 10,473,659 B2 | 11/2019 | Pulitzer et al. |
| 10,477,175 B2 | 11/2019 | Ogasawara et al. |
| 10,498,936 B2 | 12/2019 | Ehrenkranz |
| 10,527,555 B2 | 1/2020 | Pulitzer et al. |
| 10,559,081 B2 | 2/2020 | Omer et al. |
| 10,571,395 B2 | 2/2020 | Karlovac et al. |
| D879,999 S | 3/2020 | Wronko |
| 10,605,741 B2 | 3/2020 | Lu et al. |
| 10,635,870 B2 | 4/2020 | Pulitzer et al. |
| 10,636,527 B2 | 4/2020 | Pulitzer et al. |
| 10,663,466 B2 | 5/2020 | Ozean et al. |
| D886,901 S | 6/2020 | Hussey et al. |
| 10,670,533 B2 | 6/2020 | Nazareth et al. |
| 10,681,516 B2 | 6/2020 | Zin et al. |
| 10,753,932 B2 | 8/2020 | Hopper |
| 10,769,489 B2 | 9/2020 | Nahum et al. |
| 10,796,183 B2 | 10/2020 | Topal et al. |
| 10,835,122 B2 | 11/2020 | Pulitzer et al. |
| 10,890,534 B2 | 1/2021 | Pulitzer et al. |
| 10,948,352 B2 | 3/2021 | Burg |
| D915,618 S | 4/2021 | Heron |
| 10,983,065 B2 | 4/2021 | Burg |
| 10,991,096 B2 | 4/2021 | Adiri et al. |
| 11,026,624 B2 | 6/2021 | Adiri et al. |
| 11,030,778 B2 | 6/2021 | Burg et al. |
| 11,087,467 B2 | 8/2021 | Adiri et al. |
| 11,107,585 B2 | 8/2021 | Pulitzer et al. |
| 11,112,406 B2 | 9/2021 | Pulitzer et al. |
| 11,120,235 B2 | 9/2021 | Pulitzer et al. |
| D970,033 S | 11/2022 | Marcelpoil et al. |
| 2003/0108450 A1 | 6/2003 | Mainquist et al. |
| 2005/0221504 A1 | 10/2005 | Petruno et al. |
| 2007/0026530 A1 | 2/2007 | Wu et al. |
| 2007/0196862 A1 | 8/2007 | Wang |
| 2008/0287316 A1 | 11/2008 | Spivey et al. |
| 2012/0063652 A1 | 3/2012 | Chen et al. |
| 2012/0106811 A1 | 5/2012 | Chen et al. |
| 2013/0273666 A1 | 10/2013 | Chen et al. |
| 2014/0294265 A1 | 12/2014 | Chen et al. |
| 2015/0211987 A1* | 7/2015 | Burg .................... A61B 5/1172 356/402 |
| 2015/0254844 A1 | 9/2015 | Tsai et al. |
| 2015/0325006 A1 | 11/2015 | Adiri et al. |
| 2016/0139156 A1* | 5/2016 | Lakdawala ........ G01N 21/8483 435/7.92 |
| 2016/0222373 A1 | 8/2016 | Jia |
| 2016/0245793 A1 | 8/2016 | Samsoondar |
| 2016/0281150 A1 | 9/2016 | Rawlings et al. |
| 2016/0300420 A1* | 10/2016 | Li .......................... G07D 11/30 |
| 2018/0190373 A1 | 7/2018 | Pulitzer et al. |
| 2018/0196037 A1 | 7/2018 | Polwart et al. |
| 2018/0259449 A1 | 9/2018 | Poulsen et al. |
| 2018/0364224 A1 | 12/2018 | Pulitzer et al. |
| 2018/0372717 A1 | 12/2018 | Tu et al. |

(56) References Cited

U.S. PATENT DOCUMENTS

| | | | |
|---|---|---|---|
| 2019/0148014 | A1 | 5/2019 | Pulitzer et al. |
| 2019/0302009 | A1 | 10/2019 | Borich et al. |
| 2019/0376966 | A1 | 12/2019 | Pulitzer et al. |
| 2020/0126227 | A1 | 4/2020 | Adiri et al. |
| 2020/0242769 | A1 | 7/2020 | Limburg et al. |
| 2020/0286600 | A1 | 9/2020 | De Brouwer et al. |
| 2020/0319140 | A1 | 10/2020 | Saratkar et al. |
| 2021/0016280 | A1 | 1/2021 | Flesher |
| 2021/0089814 | A1 | 3/2021 | Lopes et al. |
| 2021/0142890 | A1 | 5/2021 | Adiri et al. |
| 2021/0231574 | A1 | 7/2021 | Wang et al. |
| 2022/0128455 | A1 | 4/2022 | Marcelpoil et al. |
| 2023/0296600 | A1 | 9/2023 | Rowe et al. |

FOREIGN PATENT DOCUMENTS

| | | | |
|---|---|---|---|
| EP | 3477270 | A1 | 5/2019 |
| EP | 3581921 | A1 | 12/2019 |
| EP | 3591385 | A1 | 1/2020 |
| EP | 3651162 | A1 | 5/2020 |
| KR | 101492972 | B1 | 2/2015 |
| WO | WO 2012/131386 | A1 | 10/2012 |
| WO | WO 2013/116831 | A1 | 8/2013 |
| WO | WO 2014/025415 | A2 | 2/2014 |
| WO | WO 2014/057159 | A1 | 4/2014 |
| WO | WO 2014/178062 | A2 | 11/2014 |
| WO | WO 2017/138946 | A1 | 8/2017 |
| WO | WO 2017/140686 | A1 | 8/2017 |
| WO | WO 2019/153934 | A1 | 8/2019 |
| WO | WO 2019/162496 | A1 | 8/2019 |
| WO | WO 2019/215199 | A1 | 11/2019 |
| WO | WO 2019/238500 | A1 | 12/2019 |
| WO | WO 2019/246361 | A1 | 12/2019 |
| WO | WO 2020/016616 | A1 | 1/2020 |
| WO | WO 2020/089188 | A1 | 5/2020 |
| WO | WO 2020/161238 | A1 | 8/2020 |
| WO | WO 2020/165456 | A1 | 8/2020 |
| WO | WO 2021/55127 | A1 | 8/2021 |
| WO | WO 2021/155082 | A1 | 8/2021 |
| WO | WO 2021/155103 | A1 | 8/2021 |
| WO | WO 2021/155105 | A1 | 8/2021 |
| WO | WO 2021/155153 | A1 | 8/2021 |
| WO | WO 2021/155170 | A1 | 8/2021 |

OTHER PUBLICATIONS

Deacon et al., "Identification of Acute Porphyria: Evaluation of a Conmercial Screening Test for Urinary Porphobilinogen". Annals of Clinical Biochemistry., vol. 35, No. 6, Nov. 1, 1998, pp. 726-732.

Gorchein, "Testing for Porphobilinogen in Urine," Clinical Chemistry, vol. 48, Issue 3, Mar. 1, 2002, pp. 564-566.

International Search Report and Written Opinion dated Dec. 30, 2011, in International Application No. PCT/US2011/001581, 9 pages.

International Search Report and Written Opinion dated May 21, 2012, in International Application No. PCT/US2011/059227, 9 pages.

International Search Report and Written Opinion dated Mar. 24, 2021, in International Application No. PCT/US2020/060579, 19 pages.

Mauzerall et al., "The Occurrence and Determination of S-Aminolevulinic Acid and Porphobilinogen in Urine," J. Biol. Chem. 1956, 219:435-446.

Moore et al., "A Quantitative Assay for Urinary Porphobilinogen," Clinical Chemistry, vol. 10, No. 12, 1964, pp. 1105-1111.

Roshal et al., "Rapid Quantitative Method Using Spin cols. to Measure Porphobilinogen in Urine," Clinical Chemistry, vol. 54, No. 2, Feb. 1, 2008 (Feb. 1, 2008), pp. 429-431.

Thermo Fisher: "Porphobilinogen (PBG) Test Kit", Catalogue No. TR52001, Dec. 31, 2011 (Dec. 31, 2011), XP055768704, Retrieved from the Internet: URL:https://static.thermoscientific.com/images/D03132~.pdf [retrieved on Jan. 26, 2021] the whole document.

Vogeser et al., "Evaluation of a commercially available rapid urinary porphobilinogen test," Clinical Chemistry and Laboratory Medicine, vol. 49, No. 9, Jan. 1, 2011, pp. 1491-1494.

Comstock J., "Healthy.io gets FDA nod for smartphone camera-based home urine test". Jul. 25, 2018; Retrieved from internet on Nov. 18, 2021 at: https://www.mobihealthnews.com/content/ healthyio-gets-fda-nod-smartphone-camera-based-home-urine-test in 2 pages.

healthy.io; (2020) Turning the smartphone into a medical device, downloaded from the Internet on Jan. 8, 2021, URL: https://healthy.io/services/maternity/ in 3 pages.

Min et al., "Development of a smartphone-based lateral-flow imaging system using machine-learning classifiers for detection of *Salmonella* spp". J Microbiol Meth. Sep. 1, 2021;188: 106288 in 8 pages.

Scanwell Health, "At-Home UTI Test—Know if you have a UTI in 2 minutes", downloaded Jan. 8, 2021 from https://www.scanwellhealth.com/uti in 9 pages.

International Search Report and Written Opinion dated Mar. 24, 2021 for Application No. PCT/US2020/060579 in 16 pages.

International Search Report and Written Opinion dated Jan. 24, 2022 for Application No. PCT/US2021/055963 in 9 pages.

International Search Report and Written Opinion dated Jun. 22, 2021 for Application No. PCT/US2021/025789 in 11 pages.

Becton, Dickinson and Company, "BD Receives Emergency Use Authorization for First At-Home COVID-19 Test to Use Smartphone to Interpret, Deliver Results", BD Press Release; Aug. 25, 2021; available online at https://news.bd.com/2021-08-25-BD-Receives-Emergency-Use-Authorization-for-First-At-Home-COVID-19-Test-to-Use-Smartphone-to-Interpret,-Deliver-Results; 2 pages.

\* cited by examiner

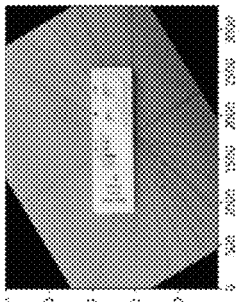
FIG. 10A FIG. 10B FIG. 10C FIG. 10D
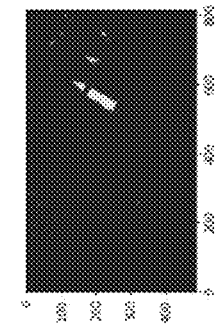
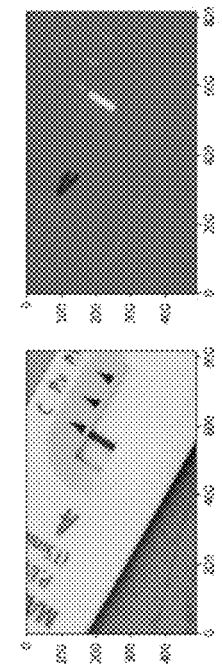
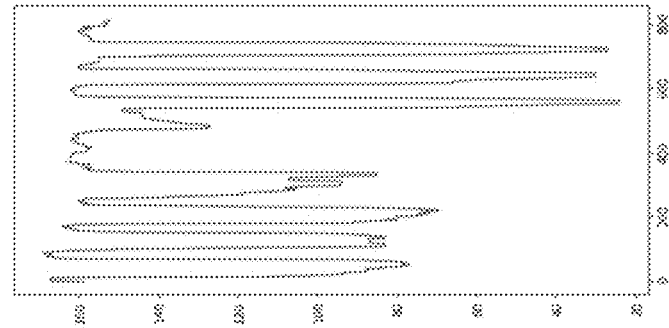
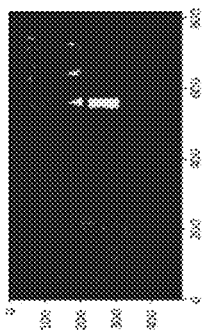
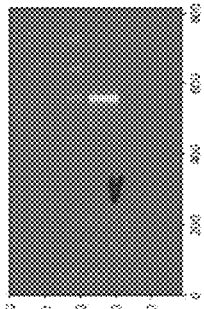
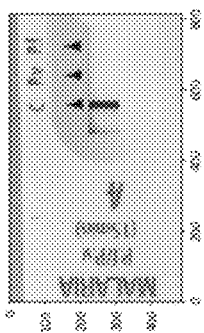
FIG. 10E FIG. 10F FIG. 10G FIG. 10H

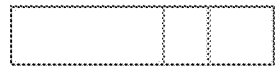

Crop Around Test Strip

FIG. 13A

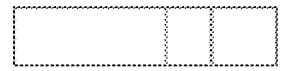

Convert to high contrast colorspace.

FIG. 13B

Split image and generate 2D array with highest contrast channel.

FIG. 13C

Calculate descriptive statistic, preferably mean, of each column of the high contrast channel.

FIG. 13D

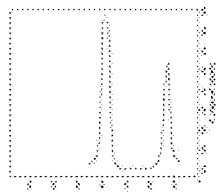

Find peaks in the 1D array generated by taking the mean of each column.

FIG. 13E

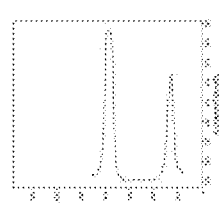

Loop list of peaks, applying simple business rules to determine the test result.

FIG. 13F

METHODS OF ANALYZING DIAGNOSTIC TEST KITS

CROSS-REFERENCE TO RELATED APPLICATIONS

This application claims priority to U.S. Patent Application Ser. No. 63/079,975 filed Sep. 17, 2020, which is incorporated herein in its entirety by this reference.

TECHNICAL FIELD

This invention relates generally to the field of diagnostic testing using computer vision-aided analysis.

BACKGROUND

Medical diagnostic testing is an important component of medical care. Many diagnostic tests incorporate immunoassay tests to confirm the presence or absence of a target analyte such as a biomarker or pathogen in a patient sample (e.g., urine, blood, saliva, sample from nasal swab, etc.). For example, one type of diagnostic test is a lateral flow immunoassay test, in which the sample is placed onto a conjugate pad or into the well of a cassette and liquid runs through a lateral flow immunoassay, which then may produce a fiducial in view of a positive chemical response to the presence of a target analyte. As another example, colorimetric diagnostic tests use reagents that undergo an apparent color change in the presence of a target analyte. However, interpretation of diagnostic test results using the naked eye may be challenging and/or subjective (e.g., in cases with very faint positive test results), which may lead to inaccurate test results.

While current diagnostic test reading devices and other clinical analyzers exist, they require customized reading equipment in order to standardize the test reading environment. Many assay reader instruments also require specialized training to operate. Accordingly, current diagnostic test reading devices require operation within a clinic, hospital, or other controlled setting so that an accurate reading may be made. Such restrictions lead to drawbacks including patient inconvenience, increased medical care costs, and limitations in widespread diagnostic testing. Accordingly, there is a need for new and improved systems and methods for diagnostic testing.

SUMMARY

In some variations, a method for analyzing a diagnostic test may include, at one or more processors, receiving an image depicting a diagnostic test, where the diagnostic test comprises a test region indicating a test result, validating the quality of the image, locating a test region image portion of the image depicting the test region of the diagnostic test; and predicting the test result based on the test region image portion.

Furthermore, in some variations, a method for facilitating analysis of a diagnostic test may include, at one or more processors, receiving one or more images depicting one or more control markings on a scan surface, where the one or more control markings are representative of one or more predetermined test results for the diagnostic test, and verifying detection of the one or more control markings in the one or more images using a least one computer vision technique.

In some variations, a system for facilitating analysis of a diagnostic test may include a scan surface comprising one or more control markings, where the one or more control markings are representative of one or more predetermined test results for the diagnostic test. The scan surface may, in some variations, further include a test placement guide indicating placement of the diagnostic test. The scan surface may, for example, be used as a background against which the diagnostic test may be imaged for analyzing diagnostic test results using one or more computer vision techniques.

Generally, in some variations, a diagnostic test kit may include a diagnostic test comprising a test region for indicating a test result, and a scan surface comprising one or more control markings, where the one or more control markings are representative of one or more predetermined test results for the diagnostic test.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 10A-10I depict an example variation of measuring and correcting orientation of a diagnostic test in an image.

FIGS. 13A-13F are schematic illustrations of portions of an example variation of a method for predicting a diagnostic test result from an image of a test region of a diagnostic test.

DETAILED DESCRIPTION

Non-limiting examples of various aspects and variations of the invention are described herein and illustrated in the accompanying drawings.

Described herein are systems and methods for analyzing diagnostic tests using computer vision techniques. The systems and methods may, for example, be used to analyze results of rapid diagnostic tests that provide a visual indication of test results (e.g., line, color change, etc.) due to the presence of a certain chemical response associated with a medical condition. The systems and methods described herein utilize computer vision-based techniques to automatically interpret results of a diagnostic test using computer vision techniques that enable easy, accurate, and reliable performance of the diagnostic test from a variety of settings, including in the home or outside of traditional healthcare settings.

Figure 1:
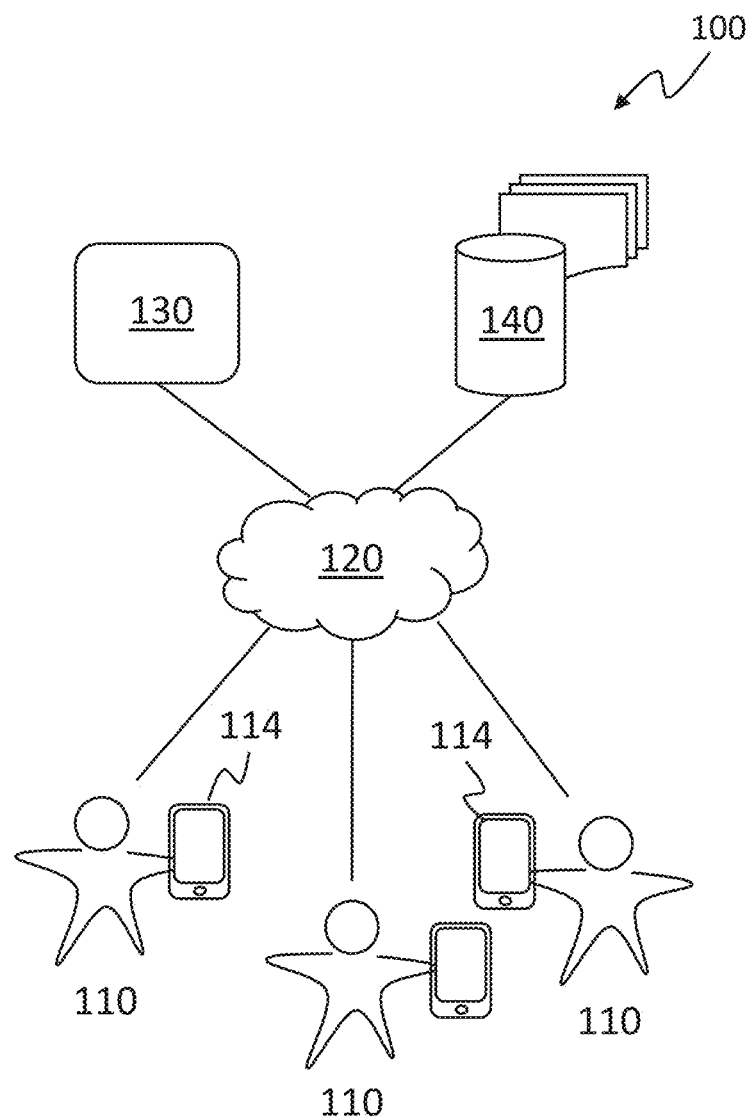
FIG. 1 is an illustrative schematic of a diagnostic platform for analyzing diagnostic tests.

Generally, as shown in FIG. 1, a diagnostic platform 100 may be used to analyze diagnostic tests associated with one or more users 110. Each user 110 may initiate and perform a diagnostic test (e.g., by applying a sample such as urine, saliva and buffer, nasal swab and buffer, or blood and buffer to the diagnostic test), then obtain at least one image of the diagnostic test such as with a mobile computing device 114 having at least one image sensor (e.g., smartphone, tablet, etc.). The mobile computing device 114 may communicate the image of the diagnostic test via a network 120 (e.g., cellular network, Internet, etc.) to a predictive analysis system 130 which may include one or more processors configured to utilize computer vision techniques to interpret test results from the image of the diagnostic test. Additionally or alternatively, at least a portion of the predictive analysis system 130 may be hosted locally on the mobile computing device 114. In some variations, the mobile computing device 114 may execute a mobile application which may provide a graphical user interface (GUI) to guide a user through obtaining and/or applying a sample to the diagnostic test, and/or guide a user through obtaining a suitable image of the diagnostic test for analysis.

Example techniques for analyzing the image(s) of the diagnostic test are described in further detail below. For example, the predictive analysis system 130 may utilize one or more features in a diagnostic test kit that support the computer vision-based interpretation of diagnostic tests, as further described below. The predicted test results may then be communicated to the user (e.g., via the mobile computing device 114, such as through a GUI on an associated mobile application), to another suitable user (e.g., medical care practitioner), to an electronic health record 140 associated with the user, other storage device(s), and/or other suitable entity.

Accordingly, the systems and methods described herein may enable diagnostic information to be quickly and easily obtained and communicated to provide insight on the medical condition of a user, which may in turn prompt suitable follow-up actions for medical care such as prescribing medication, providing medical guidance or treatment, etc. Furthermore, use of the computer vision-based techniques for diagnostic test analysis leads to greater accuracy in test interpretation compared to other current automated techniques such as template matching, which is unreliable and excessively sensitive to environmental factors such as lighting, type of imaging sensor, etc. Additionally, as further described below, the systems and methods described herein may advantageously be used to analyze a wide variety of diagnostic tests without requiring expensive, specialized hardware devices for analysis, nor any fiducials or landmarks on the diagnostic test itself.

Although the systems and methods are primarily described herein with respect to analysis of medical diagnostic tests, it should be understood that in some variations, the systems and methods may be used in other applications outside of healthcare, such as in analysis of testing of food, drink, environmental conditions, etc.

Diagnostic Test Kits

As described in further detail below, a diagnostic test kit may include one or more components for aiding analysis of a diagnostic test using computer vision techniques. In some variations, a diagnostic test kit may be configured for use with a separate (e.g., third party or off the shelf) diagnostic test. For example, a diagnostic test kit may include components configured to aid a certain type or category of diagnostic test (e.g., lateral flow immunoassay test, colorimetric dipstick test, colorimetric isothermal amplification test, or lateral flow isothermal amplification test, etc.), but omit or be packaged separately from such a diagnostic test. However, in some variations, a diagnostic test kit may include both image analysis aid(s) and one or more diagnostic tests. In other words, a diagnostic test kit may include component(s) for aiding analysis of a diagnostic test that are packaged with or otherwise supplied in conjunction with one or more suitable diagnostic tests.

Figure 2A:
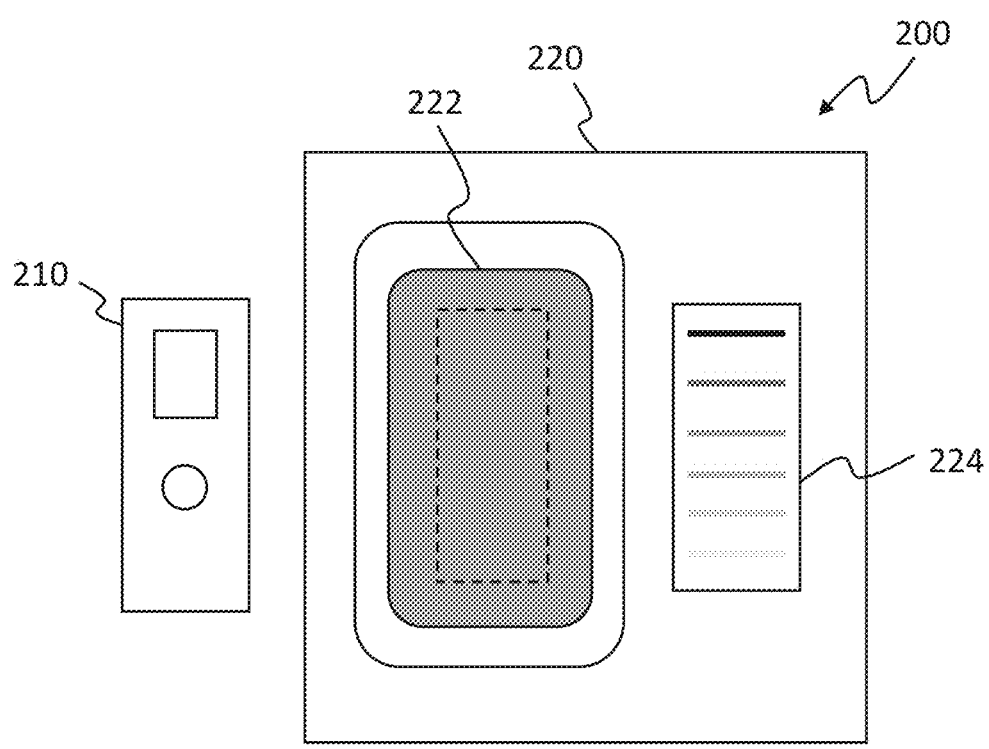
FIG. 2A is an illustrative schematic of an example variation of a diagnostic test kit for aiding analysis of a diagnostic test using computer vision techniques.

FIG. 2A depicts a schematic of an example variation of a diagnostic test kit 200 for facilitating computer vision-aided analysis of a diagnostic test. As shown in FIG. 2, the kit 200 may include at least one scan surface 220 that includes one or more various features, such as a test placement guide 222 indicating placement of a diagnostic test for imaging, and/or one or more control markings 224 that are representative of one or more possible (e.g., predetermined) test results for the diagnostic test. The test placement guide 222 and the control markings 224 may be on the same surface or on separate surfaces, as further described below. In some variations, the scan surface 220 may additionally or alternatively include other markings that function as fiducials for spatial referencing, color calibration, etc. Furthermore, the diagnostic test kit 200 may include one or more diagnostic tests 210 for use with the scan surface 220, such that the diagnostic test(s) 210 and the scan surface 220 are packaged or otherwise provided together. Alternatively, the diagnostic test kit 200 may omit a diagnostic test 210, such that the diagnostic test kit 200 may be provided as a supplementary aid to a separate diagnostic test 210, to provide support for computer vision-aided analysis thereof.

Diagnostic Test

The diagnostic test kit 200 may include (or may be configured to support analysis of) one or more suitable diagnostic tests 210 (e.g., rapid diagnostic tests). Suitable diagnostic tests include rapid diagnostic tests that depict a visual indication of a test result, such as a line, color change, or other fiducial. Example types of diagnostic tests include lateral flow immunoassay tests and colorimetric diagnostic tests (e.g., direct flow immunoassay tests, isothermal amplification tests with a paper readout, isothermal amplification tests with a colorimetric readout, etc.). For example, a lateral flow immunoassay test may include a test strip housed in a cassette with a window that frames a test region of the test strip, and in the event of a positive test result, a test result line (in combination with a control line) may be visible within the window of the cassette.

In some variations, the diagnostic test may include a high contrast material around a test region that includes test results. The high contrast may help enable more accurate identification of the outline or boundary of the test region using computer vision techniques. For example, while conventional diagnostic tests include a white cassette enclosure and a white test strip, the performance of computer vision techniques such as those described herein may be enhanced if the cassette enclosure is dark (e.g., gray or black) and the test strip is white. Accordingly, in some variations the cassette enclosure of the diagnostic test may be darker than the test strip (e.g., the cassette enclosure may be gray or black, and the test strip may be white). However, other high contrast cassette colors (e.g., bright green, bright purple) that contrast with the test strip color (and/or a scan surface such as that described below) may also be suitable. Additionally or alternatively, in some variations, the cassette material may be less reflective than the test strip. For example, even a plastic cassette material that is slightly less reflective than the test strip material may greatly enhance the ease of image segmentation such that the exact boundaries of the test strip can be easily located. In some variations, the cassette of the diagnostic test may be plastic and a light gray color, which may offer sufficient contrast with the test strip for high accuracy segmentation of the image in a wide range of lighting conditions.

Additionally or alternatively, the diagnostic test may include one or more geometrical features to enhance performance of the computer vision techniques described herein. For example, in some variations the assay window in the diagnostic test may have beveled or rounded edges, which may reduce the effect of shadows cast upon the test strip.

The diagnostic test 210, for example, be configured to receive a sample from a user such as blood, plasma, serum, urine, saliva, solubilized solids, and/or a substance from a nasal swab, which may be analyzed to assess a medical condition of the user. The diagnostic test 210 may be configured to test for a medical condition such as viral infection (e.g., influenza, hepatitis, zika virus, dengue fever, chikingunya, norovirus, coronavirus (e.g., COVID-19)), bacterial infection, parasite-caused diseases (e.g., malaria), pregnancy and/or any suitable medical condition (e.g., chronic kidney disease, porphyria, hyperoxaluria, dehydration, autoimmune conditions, inflammatory diseases, drug abuse, allergic reactions, hypercholesterolemia, or hypertriglyceridemia, etc.). In some variations, the diagnostic test 210 may include multiple test regions (e.g., multiple assay windows) to facilitate simultaneously testing for multiple medical conditions (e.g., influenza and coronavirus). The diagnostic test 210 may include, for example, two, three, four, or five or more test regions.

Sample Collection Tools

In some variations, the diagnostic test kit 200 may further include one or more sample collection tools to facilitate collection of a sample from a user. Suitable sample collection tools include, for example, nasal swabs, oral collection swabs, saliva collection containers, cups, tubes, etc. The sample collection tools may be configured to enable one or more computer vision techniques to track location and movement of the sample collection tool in order to verify, in a video of a user collecting a sample with one or more of the sample collection tools, whether a sample has been collected correctly.

For example, one or more sample collection tools may include a high contrast indicator having a high contrast color (e.g., bright green, bright purple). Additionally, or alternatively, the high contrast indicator may include another visually striking characteristic, such as fluorescence or high reflectivity. Even further, in some variations the high contrast indicator may include a computer-readable fiducial, such as an ArUco marker, WR code marker, etc. The high contrast indicator may be integrated in the sample collection tool (e.g., as a dye or coating on a portion or all of the sample collection tool), and/or may include a separate component coupled to the sample collection tool.

Figure 2B:
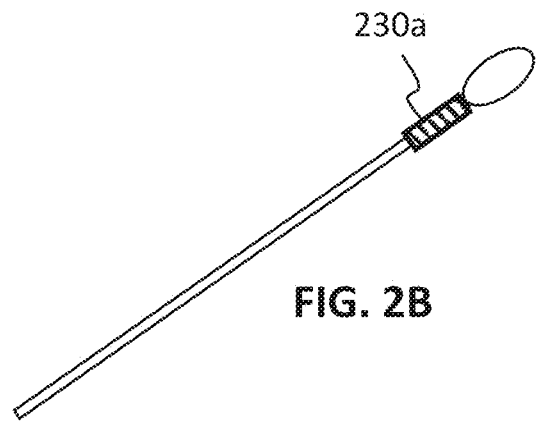
FIGS. 2B-2D are illustrative schematics of example variations of sample collection instruments with a high-contrast indicator.
Figure 2C:
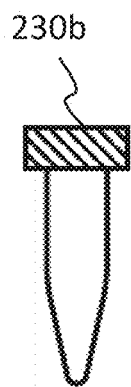
Figure 2D:
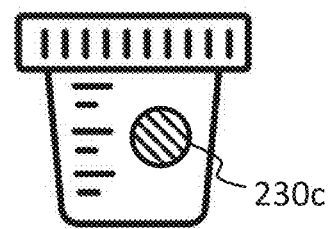

FIGS. 2B-2D are a schematic depictions of example variations of high contrast indicators. As shown in FIG. 2B, a high contrast indicator 230a may include a ring or sleeve that telescopically engages a member portion of a sample collection tool, such as the shaft of a swab (as shown in FIG. 2B) or body of a cup or tube. Alternatively, the high contrast indicator 230a may include tape that is attached around the surface of the sample collection tool. The high contrast indicator 230a may be coupled to the sample collection tool with one or more fasteners (e.g., adhesive) or through a mechanical interfit (e.g., interference fit), or included in the manufacture of the collection tool as a dye for the entire tool or dye for a specific region or component of the tool, etc. The indicator may be high contrast along any one or more regions of the electromagnetic spectrum including visible light/color, infrared, ultraviolet, etc. As an illustrative use example, the high contrast indicator 230a may be engaged on the shaft of a nasal swab proximal to the distal flocking that is inserted into the nasal cavity of a user. The high contrast indicator 230a is highly visible in video and may be tracked to enable determination of whether the swab was inserted into the nostril or oral cavity of the user to the correct depth. In some variations, multiple high contrast indicators of the same or different high contrast features may be arranged along the length of the collection swab or other sample collection tool. Multiple such high contrast indicators may, for example, be used to determine depth of swab insertion in a video of the user collecting the same, and/or provide guidance to the user to improve sample collection technique (e.g., instruct the user to insert the swab deeper).

In some variations, a functional component of the sample collection tool may include a high contrast indicator. For example, as shown in FIG. 2C, a sample collection vessel (e.g., cup, tube) may include a high contrast indicator 230b in the form of (or coupled to) a vessel cap. Additionally or alternatively, in some variations, a high contrast indicator may include a sticker that is coupled to a surface of the sample collection tool, or included in the manufacture of the collection tool as a dye for the entire tool or dye for a specific region or component of the tool, etc. The indicator may be high contrast along any one or more regions of the electromagnetic spectrum including visible light/color, infrared, ultraviolet, etc. For example, as shown in FIG. 2D, a sample collection vessel (e.g., cup, tube) may include a high contrast indicator 230c sticker that is applied to a surface of the sample collection vessel. Such high contrast indicators may be tracked similar to that described above, and their positions and/or orientations may be analyzed in order to determine whether a user has obtained a sample with a correct procedure.

In some variations, motion of the sample collection tool may be tracked with respect to the user's face (which may be detected using suitable facial recognition approaches) and/or another body part of the user (e.g., finger, hand, arm, etc.) to determine whether the user has performed a sample collection procedure appropriately. Additionally or alternatively, shape recognition and/or tracking may be performed using a depth camera (e.g., infrared camera with 3D depth mapping) and/or other suitable sensors (e.g., proximity sensors) to identify and/or track a sample collection tool, to similarly determine whether a user has performed a sample collection procedure appropriately.

Scan Surface

As described above, the diagnostic test kit 200 may include one or more scan surfaces 220 which may be placed behind any suitable diagnostic test as an aid for computer vision-based analysis. The scan surface may, for example, be located on a card, tray, mat, pedestal, housing, instruction booklet, or any suitable physical structure configured to receive a diagnostic test. The scan surface may be formed on paper, plastic, cardboard, or other suitable material.

As shown in FIG. 2A, one or more scan surfaces 220 may include a test placement guide 222 indicating placement of a diagnostic test against the scan surface for imaging, and/or one or more control markings 224 that are representative of one or more predetermined test results for the diagnostic test. Various other fiducials may additionally or alternatively be included on the one or more scan surfaces to aid computer vision techniques, as further described below.

Any of the visual features on the scan surface (e.g., test placement guide, spatial markers, calibration markers, control markings, other fiducials, etc.) may be printed or otherwise applied directly onto the scan surface or on a decal that is applied to the scan surface. For example, the visual features may be printed in ink (e.g., color ink, black ink, fluorescent ink, etc.), paint, and/or laser jet toner, etc. In variations in which some or all visual features are printed in fluorescent ink, the fluorescent ink may include, for example, an ink including europium, rhodamine, fluorescein, alexa fluor, quantum dots, and/or fluorescent nanoparticles. Printing visual features on the scan surface with fluorescent inks may, for example, enable the diagnostic testing kit to be compatible with diagnostic assays that use a fluorescent readout mechanism (e.g., products with fluorescent particles or dyes, which require a specialized reader instrument). In some variations, the visual features may be printed in a digital printing process, a plate printing process, and/or other suitable printing process.

Test Placement Guides

In some variations, a scan surface may include a test placement guide that provides an indication of where a user should place a diagnostic test in order to be imaged and analyzed. The test placement guide may include one or more features to aid automated analysis of the diagnostic test.

As shown in the schematic of FIG. 2A, a test placement guide 222 may include a background color that is high contrast relative to the diagnostic test to be imaged. The high contrast background may help ensure that the outline of the diagnostic test may be reliably detected by computer vision techniques. For example, many diagnostic tests are white (e.g., in a white cassette housing). Accordingly, for these and/or other light-colored diagnostic tests, the test placement guide 222 may include a dark region (e.g., black or dark gray) or brightly colored region (e.g., bright green or bright purple, etc.) that strongly contrasts with the diagnostic test.

The bounded area of the contrasting background may be larger than the bounded area of the diagnostic test intended to be imaged (e.g., providing a margin of contrasting background that is at least 0.1 cm, between about 0.1 cm and about 5 cm, between about 0.1 cm and about 1 cm, between about 1 cm and about 2 cm, between about 2 cm and about 5 cm, or any other suitable margin, or a certain percentage of the higher of either the test length or width such as 10%, 20%, 50%, or any other suitable margin). However, the background area may be limited so as to not impact the ISO/exposure time adjustment of the image sensor (e.g., too much black in a background can cause some image sensors to overcompensate by adjusting ISO so high that it results in saturation of the white color in some sections of the imaged diagnostic test). When an imaged diagnostic test is placed onto a high contrast background, the outline of the diagnostic test may be identified in the image through techniques such as contour detection. In this manner, the outline of any diagnostic test that fits within test placement guide 222 may be determined. In other words, the diagnostic test determination may be performed independent of any custom marking or other fiducials on the diagnostic test itself. Accordingly, the high contrast background of the scan surface may advantageously enable the diagnostic test kit to be more versatile, so as to support a greater variety of diagnostic tests.

Furthermore, in some variations the test placement guide 222 may include other markings and/or other features to instruct placement of a diagnostic test on the guide 222. For example, in some variations the test placement guide 222 may include text (e.g., "Place test here"), a graphical representation of a diagnostic test (e.g., line drawing) or boundary thereof, and/or suitable symbols (e.g., arrows) to suggest proper position and/or orientation of a diagnostic test against the scan surface. Such additional guidance may, for example, be visual (e.g., printed directly on the scan surface, printed on a decal affixed to the scan surface, etc.) and/or textural (e.g., indentations, raised features, etc.).

Figure 3A:
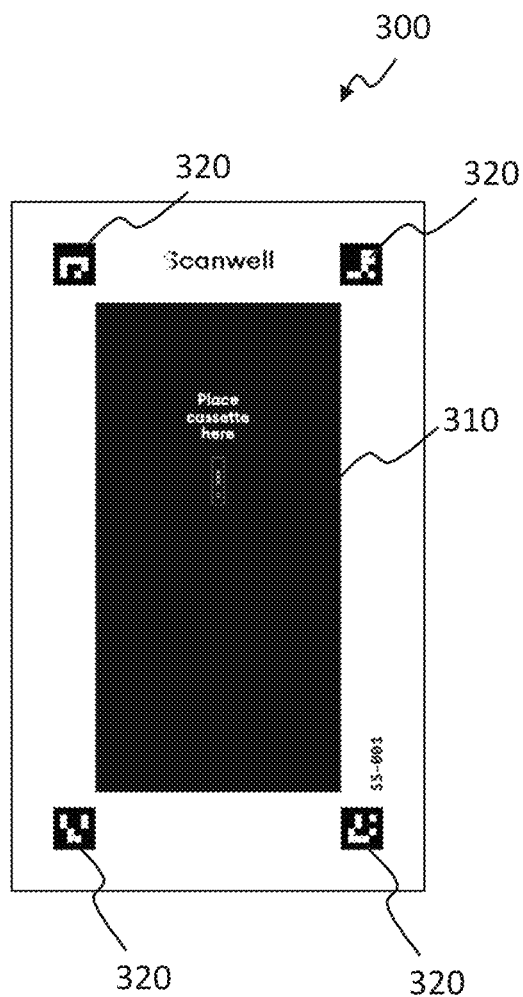
FIGS. 3A and 3B depict example variations of a scan surface for receiving a diagnostic test to be imaged.

An example variation of a scan surface 300 (e.g., scan card) is shown in FIG. 3A. As shown in FIG. 3A, the scan surface 300 includes a test placement guide 310 that includes a dark-colored background configured to be high contrast relative to a light-colored diagnostic test to be placed on the test placement guide 310. The test placement guide 310 also includes instructive text ("Place cassette here") and a graphical representation of a lateral flow assay test cassette to suggest proper orientation of the cassette relative to the scan surface. For example, the graphical representation shown in FIG. 3A includes an outline of a cassette with its sample intake (pictured as a short line) directed toward the lower edge of the scan surface 300, and its test region (pictured as a longer line) directed toward the upper edge of the scan surface 300. Accordingly, the test placement guide 310 includes a suggestion to orient the test cassette in a manner similar to diagnostic test (T) shown in FIG. 3B.

Spatial Markers

In some variations, the scan surface may include one or more spatial markers that function to help facilitate spatial locating and/or identification of the spatial orientation of the diagnostic test and/or a test region (a region of the test displaying test results) within the image. In some variations, the spatial markers may be located in and/or around the test placement guide (that is, a region of the scan surface expected to receive a diagnostic test) in an arrangement that defines a boundary of the diagnostic test in the image. By identifying the spatial markers, this boundary around the diagnostic test may be identified, thereby enabling cropping of image to isolate the diagnostic test for further analysis without interference from the background of the image. For example, the scan surface may include at least three spatial markers that form vertices of a bounded area. Generally, the spatial markers may include any suitable fiducial, such as ArUco markers, QR code markers, other computer-readable markers, or custom markers with sufficiently contrasting visual characteristics. Additional details of use of spatial markers during image analysis are described in further detail below.

Figure 3B:
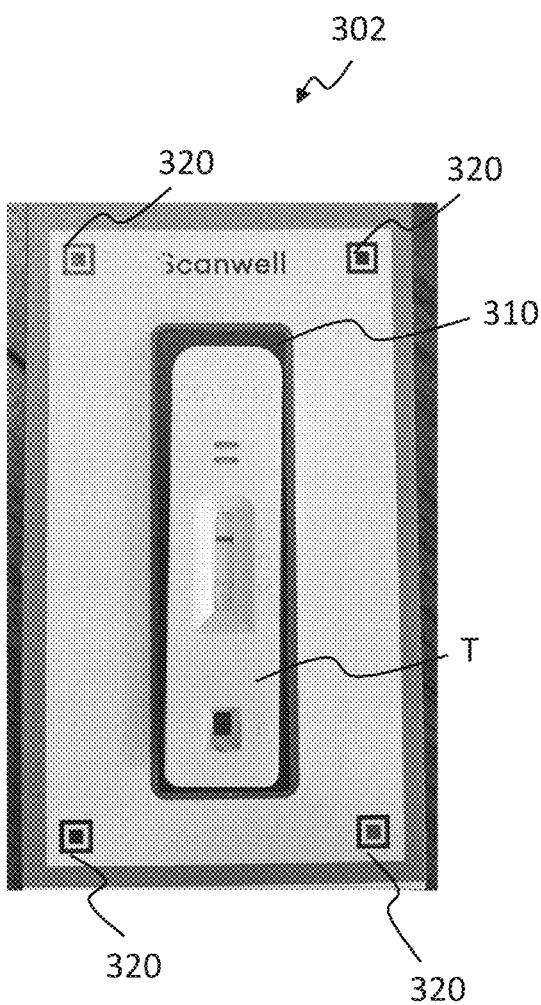

As shown in the example depicted in FIG. 3A, the scan surface 300 may include four spatial markers 320 that arranged at corners of a bounded rectangular area around the test placement guide 310. In some variations, three of such spatial markers may be sufficient to define the bounded rectangular area by defining a width and a length of the rectangular area. Although the scan surface 300 is depicted in FIG. 3A as including four spatial markers forming a rectangular boundary that provides guidance for a rough image crop, it should be understood that in other variations, the scan surface may include any suitable number of spatial markers forming any suitable shape (e.g., three markers, five markers, six markers, etc.). Furthermore, while the scan surface 300 shown in FIG. 3A includes ArUco markers functioning as spatial markers, it should be understood that in other variations the spatial markers may have any suitable form. For example, FIG. 3B depicts an example variation of a scan surface 302 that is similar to the scan surface 300 depicted in FIG. 3A, except that the spatial markers in the scan surface 302 are QR markers instead of ArUco markers.

Calibration Markers

In some variations, the scan surface may include other suitable markers for calibration or other reference. For example, the scan surface may include standard color and/or grayscale markings that may function as a reference for automatic color correction (e.g., white balance) by an image sensor, so as to reduce the influence of illuminant conditions that may interfere with accurate test result interpretation. Additionally or alternatively, such color calibration markers may appear on any suitable surface, such as a surface that is separate from the scan surface for receiving the diagnostic test. For example, color calibration markers may be present on a separate calibration card that may be referenced separately and prior to imaging the diagnostic test on the scan surface.

Additionally or alternatively, the scan surface may include alignment markers that may function to indicate a predetermined geometry and orientation of the diagnostic test on the assay. Such alignment markers may, for example, be similar to markings on the test placement guide 222 as described above and/or as shown in FIG. 3A as described above.

Control Markings

As shown in FIG. 2A, in some variations, the scan surface 220 may include one or more control markings 224 that are representative of one or more predetermined test results for the diagnostic test. For example, the control markings may include shapes having a specific color, thickness, and/or intensity that correspond to the expected shape, color, thickness, and/or intensity of the test results and/or test control markings in the diagnostic test. In some variations, the control markings 224 may include at least one marking that corresponds to the lower limit (or near the lower limit) of detection or quantitation of the diagnostic test.

The control markings 224 may function to help ensure that the camera is able to generate an image of adequate quality that permits detection of a fiducial indicating a test result, including a faintly visible fiducial. For example, the control markings 224 may be used to help ensure that the camera has sufficient resolution, sufficient image sensor quality, and/or sufficient autofocus, autoexposure, and/or color/white balancing settings and/or abilities. If each of the one or more control markings 224 is detected in an image of the control markings by the diagnostic test platform's computer vision techniques, it is likely that the platform is capable of correctly interpreting the test result of the diagnostic test, including positive and faint positive results.

Appearance of the control markings may vary depending on the type of diagnostic test with which the control markings are associated with. For example, for a diagnostic test such as a lateral flow immunoassay test, the control markings 224 may include a set of lines. As shown in the schematic of FIG. 2A, the lines may vary in thickness, color, reflectivity, and/or hue (e.g., darkness), and at least some of the lines may be similar in size, shape, and/or color to the expected control lines and/or test result lines that appear on the lateral flow immunoassay test. For example, in some variations the printed controls may include black or gray lines (e.g., of varying intensity in grayscale). As another example, in some variations the printed controls may include lines of varying colors (e.g., red, blue, green, etc.). If each of the lines is detected by the computer vision techniques, it is likely that the computer vision techniques are able to correctly interpret test results in images of the diagnostic test.

Figure 4A:
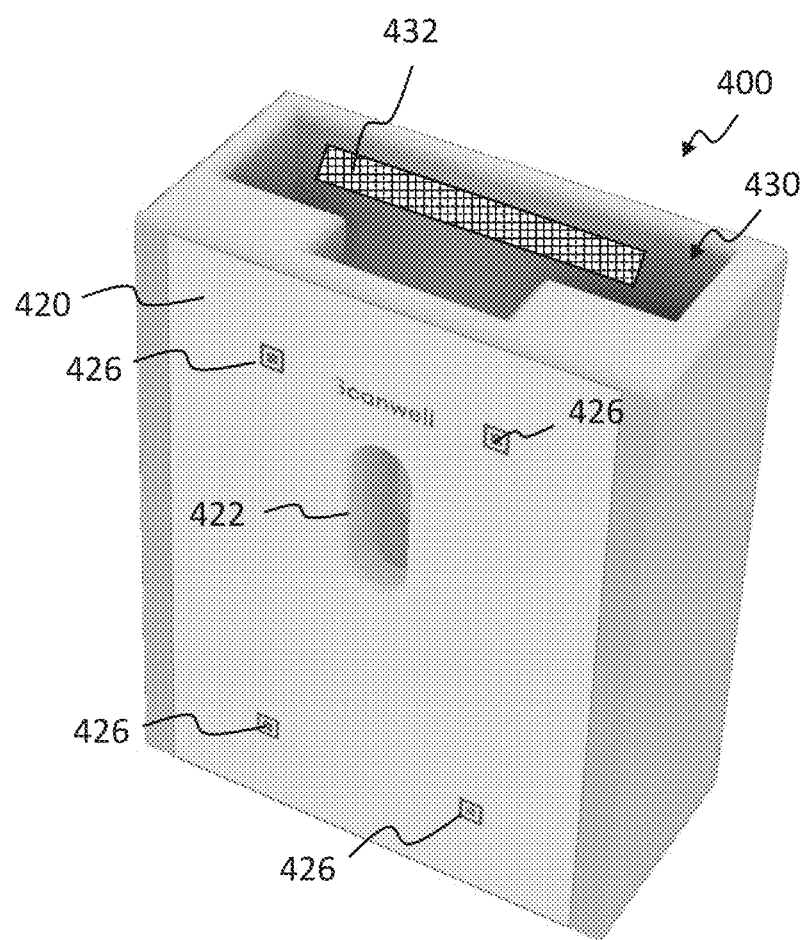
FIGS. 4A and 4B depict example variations of a housing in a diagnostic test kit.
Figure 4B:
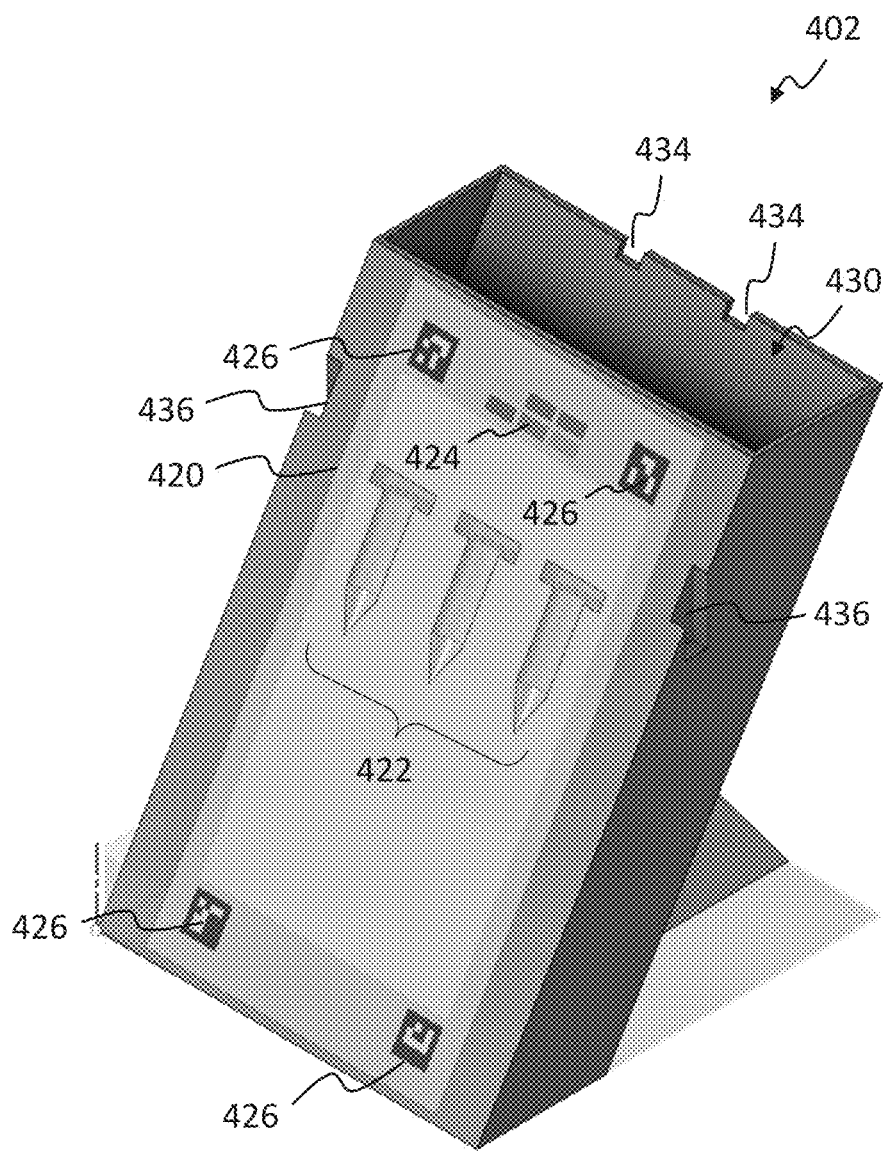

As another example, for a diagnostic test such as a colorimetric immunoassay test, the one or more control markings may include a set of colored markings. As shown in FIG. 4B, for example, a scan surface 420 may include a series of control markings 424 including colored boxes. Similar to that described above, the color of each box may be representative of a predetermined test result for the diagnostic test (e.g., positive or negative test, positive control, negative control, etc.). Additionally or alternatively, the control markings may include black or gray boxes (e.g., of varying intensity in grayscale). If each of the colored, black, and/or gray boxes is detected by the computer vision techniques, it is likely that the computer vision techniques are able to correctly interpret test results in images of the diagnostic test.

Although in some variations, as shown in FIGS. 2A and 4B, the control markings may include geometric shapes arranged in an array (e.g., 1D array, 2D array), it should be understood that the control markings may incorporate the appropriate control markings as part of any suitable design. For example, the control markings may be artfully arranged in a suitable graphical design (e.g., graphical icons such as a wave, house, tree, simple lines, etc.), which may contribute to a more aesthetically pleasing design of the diagnostic testing kit.

Similar to other visual features of the scan surface as described above, the control markings may be printed onto a card, paper, mat, tray, housing (e.g., box), and/or other suitable surface. In some variations, the control markings may be located proximate (e.g., adjacent) a test placement guide on the scan surface, such that the diagnostic test and the control markings may be in the same field of view of a camera (to be imaged together) imaging the diagnostic test. In some variations, some or all control markings may be located on a separate component than the component that receives the diagnostic test, as the control markings may be imaged separately from (e.g., prior to) imaging the diagnostic test. Analysis of the control markings prior to imaging the diagnostic test may, for example, help enable a user to determine whether a specific camera device is adequate prior to consuming a diagnostic test, thereby avoiding waste of a diagnostic test in the event that the user's intended camera device is not able to obtain an image of adequate quality for analysis. Other details of the use of control markings to verify camera quality are described further below.

Encoded Information

In some variations, the diagnostic test kit may include one or more computer-readable codes for easy and reliable identification and/or traceability of the test kit and/or its components. For example, the diagnostic test kit may include a QR code, a bar code, and/or other suitable markings that encode information associated with the diagnostic test kit, such as expiration date, product SKU, lot number, and/or the like. Additionally or alternatively, the computer-readable code may encode routing information that directs communication software (e.g., in a mobile application executed on a mobile computing device) to transmit test results and/or any associated metadata (e.g., name, date/time of test, information relating to calibration or image quality control, etc.) to a particular designated destination, such as a specific server, cloud service, email address, mobile number, etc.

In some variations, one or more such computer-readable codes may be printed or otherwise located on a scan surface, and may be proximate to a test placement guide so as to be in the same field of view as the diagnostic test and/or other markings on the scan surface. Alternatively, one or more computer-readable codes may be on a separate scan surface (e.g., on a housing as described below, on a separate instruction booklet, etc.).

Color References

Additionally or alternatively, in some variations the scan surface may include a color reference array or other pattern that includes example colors for use in analyzing test results of a colorimetric diagnostic test. For example, a color reference array may include a group of colored blocks or other icons, each of which may correspond to a particular test result, and may be intended for assessing color of an assay with a particular test result (e.g., analyte concentration). The color reference array may include colored icons arranged in a grid, an artful arrangement, or any suitable pattern. In some variations, the control markings as described above may additionally function as a color reference array for purposes of test analysis. Additionally or alternatively, the color reference array may be similar to those described in U.S. Pat. Nos. 8,655,009 and 8,911,679, each of which is incorporated herein by this reference.

Housing

In some variations, the diagnostic test kit may include a housing. For example, as shown in FIG. 4A, in some variations a diagnostic test kit may include a housing 400 that includes at least one compartment 430 that may receive one or more diagnostic test kit components. In some variations, the housing may be useful for diagnostic tests that lack a plastic enclosure or cassette. The compartment 430 may, for example, be configured to store components such as one or more tools for sample collection and/or sample manipulation (e.g., swabs, cups, tubes, centrifuge tubes, capillary tubes, disposable pipette, other sample vessels, test strips, syringes, needles, syringe filters, alcohol wipes, reagents, etc.). In some variations, components may be organized in trays (e.g., injection molded trays with cavities shaped to correspond to components), boxes, and/or in any suitable manner in the compartments 430. The components may be removed for use during the testing process.

Additionally or alternatively, in some variations the housing may include a scan surface 420 that is similar to scan surfaces described above, and the housing may function as an assay stand. For example, as shown in FIGS. 4A and 4B, the scan surface 420 may include a high contrast background, spatial markers 426, and/or other suitable calibration markers that help computer vision techniques to locate a diagnostic test that is placed against the scan surface 420. Furthermore, as shown in FIG. 4B, the scan surface 420 may include one or more control markers 424, as described above. In some variations, as shown in FIG. 4B, the scan surface 420 may be sloped or angled upward (e.g., due to geometry of the housing, orientation of the housing with a kickstand such as that shown in FIG. 4E for an assay stand, etc.), which may improve illumination of the diagnostic test on the scan surface 420, avoid shadows, etc. In some variations, the angle may be fixed, while in some variations the angle may be adjustable, such as with an adjustable kickstand.

However, the scan surface 420 shown in FIGS. 4A and 4B may include a test placement guide 422 including at least one receptacle (e.g., cutout or indentation) configured to receive a diagnostic test for analysis. For example the receptacle may be shaped and sized to cradle a diagnostic test (e.g., cassette, sample vessel, etc.). Furthermore, in some variation the receptacle may share a wall (or membrane, etc.) with the compartment 430 such that in variations in which a heating device is arranged in the compartment 430 (as described in further detail below), heat may transfer from the heating device across the shared wall to a diagnostic test positioned in test placement guide 422. The diagnostic test may be secured in the receptacle via a mechanical interfit such as a snap fit, adhesive, etc. such that it is held in place on the scan surface 420. The test placement guide 422 may include a single receptacle as shown in FIG. 4A, or multiple receptacles as shown in FIG. 4B. For example, the test placement guide 422 shown in FIG. 4B may include three receptacles for receiving vessels providing a positive control, a negative control, and a test result. However, it should be understood that in other variations the test placement guide 422 may include any suitable number of receptacles of any suitable shape (e.g., for receiving conical sample tubes, pipettes, capillary tubes, cuvette, etc.). Additionally or alternatively, other cutouts (e.g., notches 436) or other suitable mounting features may formed in the side or other suitable surface of the housing, so as to provide a mount point for components such as a cuvette holder, etc.

Figure 4C:
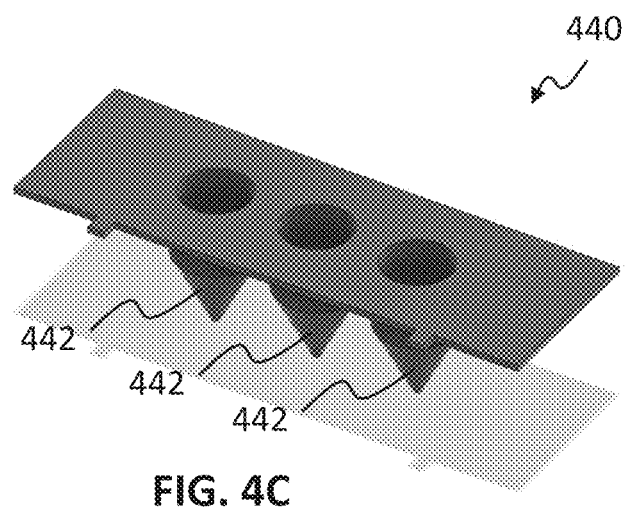
FIGS. 4C and 4D depict perspective views of an example variation of a housing cover for a diagnostic test kit.
Figure 4D:
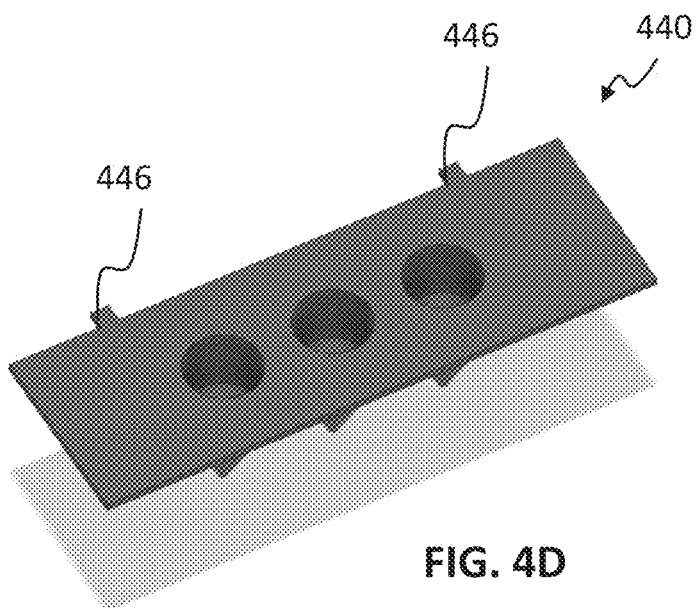
Figure 4E:
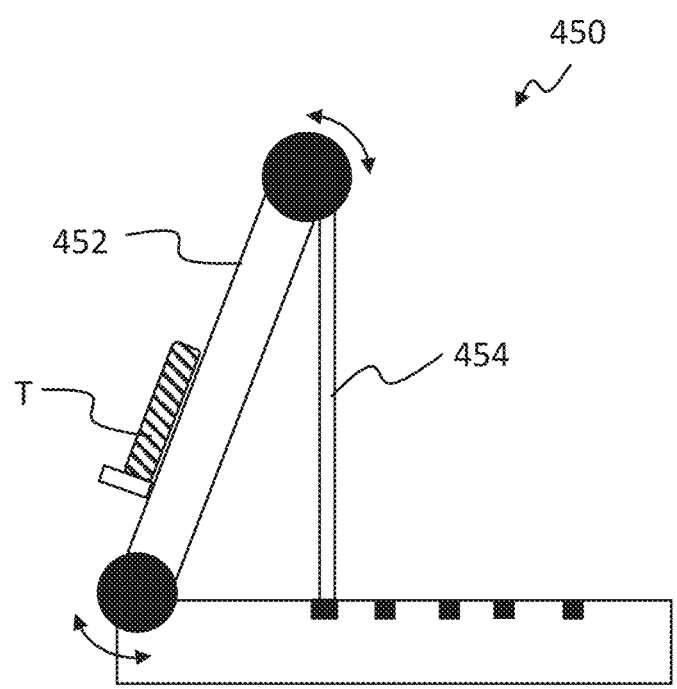
FIG. 4E is an illustrative schematic of an example variation of an assay stand in a diagnostic test kit.

The housing may, in some variations, include a cover for covering the compartment and/or enclosing the housing. For example, FIGS. 4C and 4D depict an example variation of a housing cover 440 that may couple to a housing such as housing 402 depicted in FIG. 4B. The housing cover 440 may include one or more alignment features 446 that are configured to engage with alignment features 434 on the housing 402, which may help orient and/or secure the housing cover 440 on the housing 402. In some variations, the housing cover 440 may include one or more receptacles 442 for receiving diagnostic test components (e.g., conical tubes for reaction mixtures, etc.). The location of these receptacles 442 may, for example, be advantageous in variations in which heat from a heating device (as described in further detail below) in the compartment 430 is used to warm items in the receptacles 442. In some variations, the receptacles 442 may be used to warm sample vessels (e.g., positive control, negative control, test result) for a predetermined period of time (e.g., 30 seconds), and then the warmed vessels may be transferred to an imaging area such as the scan surface 420.

The housing may be made in any various suitable manners. For example, the housing may be injection molded, 3D printed, milled, folded, and/or formed in any suitable process. The housing may include any suitable materials, such as plastic, paper (e.g., wax paper), cardboard, metal, etc.

Heating Device

In some variations, the diagnostic test kit may include a heating device. Many diagnostic tests utilize an isothermal amplification step, for which the heating device may provide heat. As shown schematically in FIG. 4A, the heating device 432 may be located in the compartment 430 of the housing, so as to warm items placed in one or more receptacles in and/or around the housing. For example, when placed in the compartment 430, the heating device may be configured to warm diagnostic test(s) (including test samples, controls, etc.) on a scan surface 420 and/or housing cover 440. However, one or more heating devices may be arranged in any suitable location (e.g., on the exterior of the housing, such as on a front surface, back surface, bottom surface, side surface, etc.). Even further, in some variations the heating device may be separate from the housing, such as in a standalone structure configured for warming test samples.

In some variations in which the heating device 432 is in the compartment 430 of the housing, the housing may include features to enhance heat transfer between the heating device 432 and the diagnostic device and/or other vessels for warming. For example, the housing may include channels or cavities configured to maximize surface area contact between the heating device and the diagnostic device. As another example, the housing may additionally or alternatively include thermally conductive material (e.g., aluminum or other conductive material) to function as conduits of heat between the heating device and desired locations for warming.

The heating device may include any suitable kind of heating mechanism. For example, the heating device may include a water-activated quicklime heater, an air-activated heater (e.g., with cellulose, iron, activated carbon, or other suitable substance that produces heat from an exothermic reaction upon exposure to air), electrical heater, or other chemical heater. In some variations, the heating device may reach temperatures over about 65° C. for use with LAMP, rolling circle amplification, NEAR, tadpole and other isothermal amplification reactions. The heating device may additionally or alternatively be used to perform cell lysis and/or other heating steps critical for some diagnostics tests.

Other Imaging Aids
Assay Stand

In some variations, a diagnostic test kit may additionally or alternatively include a stand configured to orient the scan surface and the diagnostic test at a suitable angle to improve illumination of the diagnostic test and achieve a better image of the diagnostic test. The assay stand may be similar to the angled housing 402 described above with respect to FIG. 4B, except that the assay stand may omit a housing compartment. In some variations, the stand may be useful for diagnostic tests that lack a plastic enclosure or cassette. As shown in the illustrative schematic of FIG. 4E, the assay stand 450 may, for example, include a tray or other holder 452 that may include a scan surface similar to that described above (e.g., with alignment markers) for receiving a diagnostic test (T). The stand may be configured to angle the diagnostic test upwards and/or reflect ambient light upward toward the assay in order to improve the homogeneity of lighting on the diagnostic test. For example, the stand may be configured to angle the diagnostic test at an angle between about 10° and about 80°, between about 25° and about 65°, between about 35° and about 55°, or about 45°, etc. The scan surface may be angled due to an angled face of the stand, and/or due to an angle of the stand relative to a level surface. The angle may be fixed such as with a static angled bracket or other construction. Alternatively, the angle may be adjustable such as with an angled kickstand (e.g. as kickstand 454 shown in FIG. 4E).

Fluorescence-Related Accessories

In some variations, a diagnostic test kit may include fluorescence-related accessories to assist in imaging. For example, a diagnostic test kit may include accessories to be compatible with diagnostic tests that use a fluorescent readout mechanism (e.g., products with fluorescent particles or dyes). In some variations, a diagnostic test kit may include one or more excitation light sources (e.g., ultraviolet (UV) light sources) for exciting fluorescent particles or dyes in a diagnostic test. Additionally or alternatively, a diagnostic test kit may include one or more suitable UV filters, to be placed between the diagnostic test and the camera during imaging, to facilitate the imaging of fluorescent light emitted from the diagnostic test kit, for test analysis purposes.

It should be understood that variations of the diagnostic test kits may include any suitable combination of the components described herein. Furthermore, in some variations certain components of the test kit may be reusable (e.g., assay stand, fluorescence-related accessories) and be repeatedly used with multiple disposable components (e.g., multiple diagnostic tests). Alternatively, in some variations all components of the diagnostic test kit may be designated for single use.

Methods of Analyzing a Diagnostic Test

Figure 5:
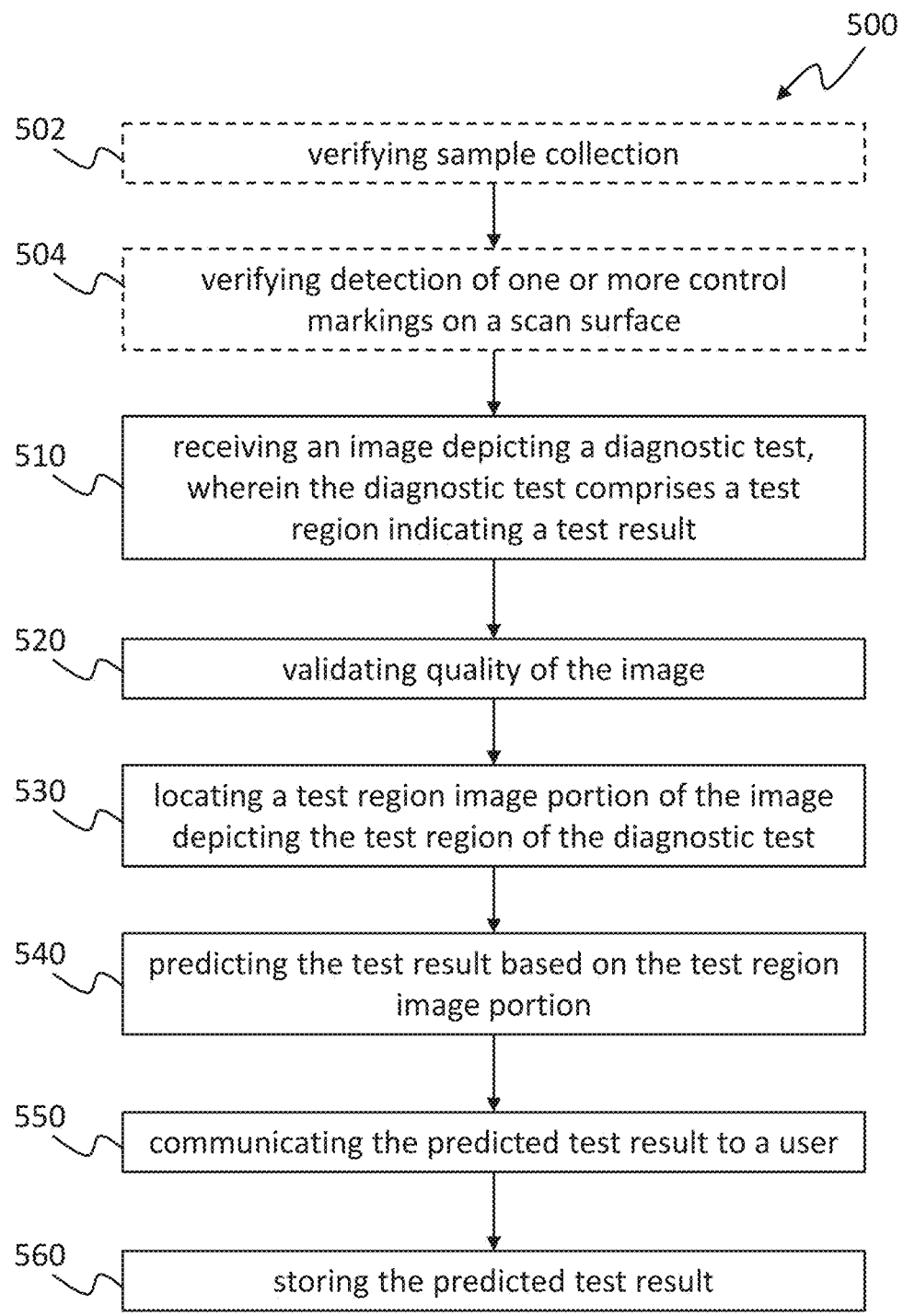
FIG. 5 depicts a flowchart of an example variation of a method for analyzing a diagnostic test.

As shown in FIG. 5, a method 500 for analyzing a diagnostic test may include, at one or more processors, receiving an image depicting a diagnostic test 510 where the diagnostic test includes a test region indicating a test result, validating quality of the image 520, locating a test region image portion of the image 530 depicting the test region of the diagnostic test, and predicting the test result based on the test region image portion 540. Furthermore, in some variations, the method 500 may further include communicating the predicted test result 550 to a user or other entity, and/or storing the predicted test result 560 (e.g., in a user's electronic health record, in a user account associated with the diagnostic platform, etc.). In some variations, the method may include verifying sample collection 502 (before, during, or after image analysis to determine test result), using techniques such as that described above with references to FIGS. 2B-2D. Furthermore, in some variations the method may include verifying detection of one or more control markings on a scan surface 504, which may, for example, be used to assess camera quality used to obtain an image for diagnostic test analysis.

In some variations, the method 500 may be used in conjunction with diagnostic test kits such as those described above (or components thereof). The method 500 may be performed locally such as on a mobile computing device (e.g., mobile application executed on the computing device and is associated with the diagnostic platform), and/or remotely such as on a server (e.g., cloud server).

Verifying Detection of Control Markings

Figure 7A:
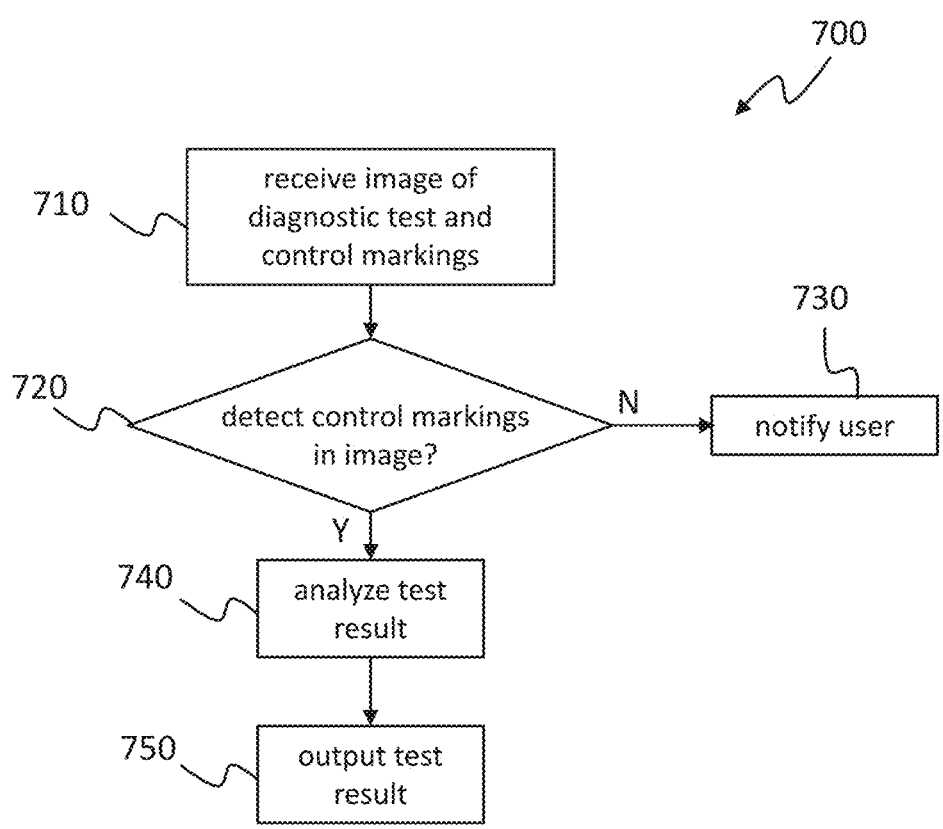
FIGS. 7A and 7B depict flowcharts of example variations of a method for facilitating analysis of a diagnostic test with the use of control markings.

In some variations, the method may include assessing the quality of the camera and/or image sensor (and/or imaging conditions) to be used for obtaining an image of the diagnostic test for analysis. For example, as shown in FIG. 7A, a method 700 for facilitating analysis of a diagnostic test may include receiving an image of a diagnostic test and one or more control markings (710). Control markings may include suitable markings that are representative of one or more predetermined test results for the diagnostic test, as described in further detail above. Computer vision techniques may assess whether all (or a sufficient portion) of the control markings may be detected in the image (720). If not all of the control markings are detected in the image, then the user may notified of the error (730). For example, a suggestion may be provided to the user to try a different camera, change one or more camera settings, adjust one or more environmental factors, or any combination thereof, etc. If the control markings are detected in the image, then the image may be further analyzed to predict the diagnostic test result (740), and the test result may be output or otherwise communicated (750) such as that as described below.

Figure 7B:
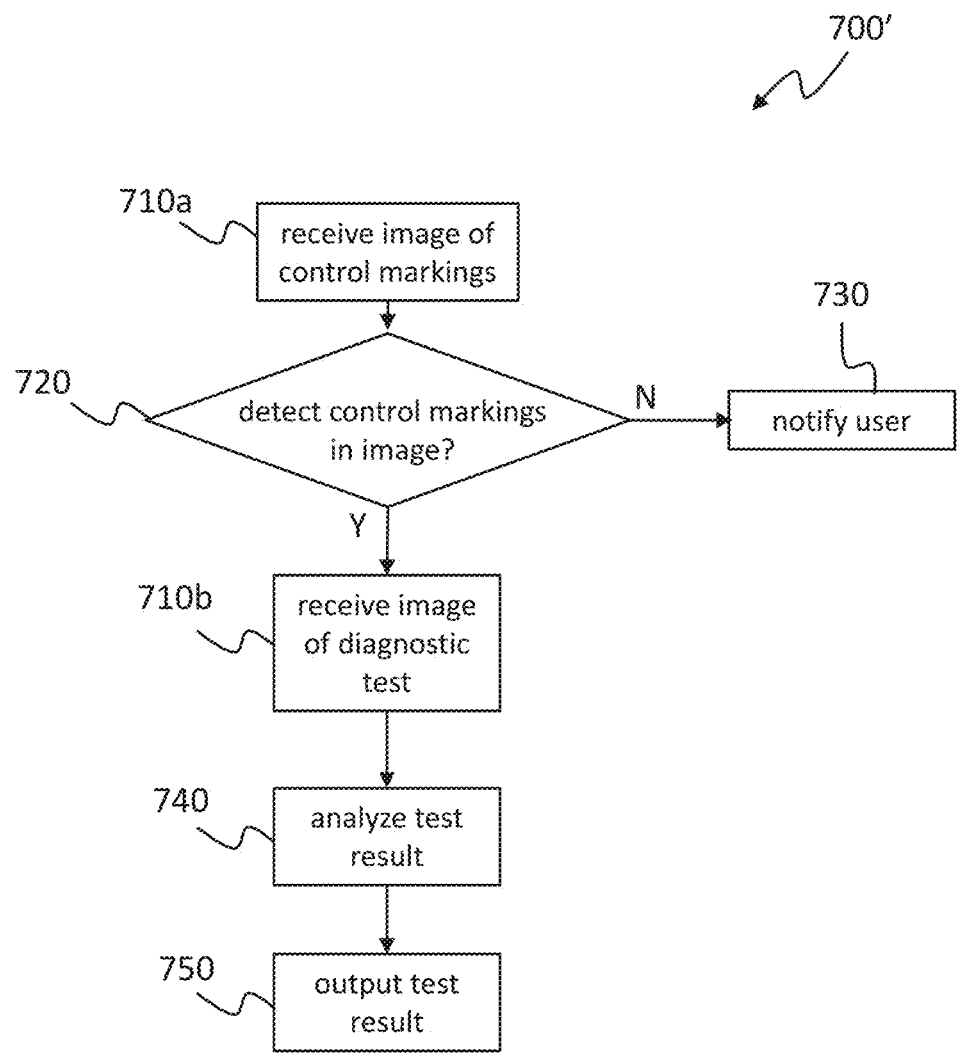

Although the method 700 depicted in FIG. 7A utilizes an image that includes both the diagnostic test and the control markings, in some variations separate images may provide this information. For example, as shown in FIG. 7B, a method 700' for facilitating analysis of a diagnostic test may include receiving a first image of one or more control markings (710a) and computer vision techniques may assess whether all or a sufficient portion of the control markings may be detected in the first image (720). If not all of the control markings are detected in the image, then the user may be notified of the error (730) as described above. If the control markings are detected in the image, then a user may be prompted to take a second image that depicts the diagnostic test (710b). The second image may then be further analyzed to predict the diagnostic test result (740) and output or otherwise communicated (750).

Figure 8A:
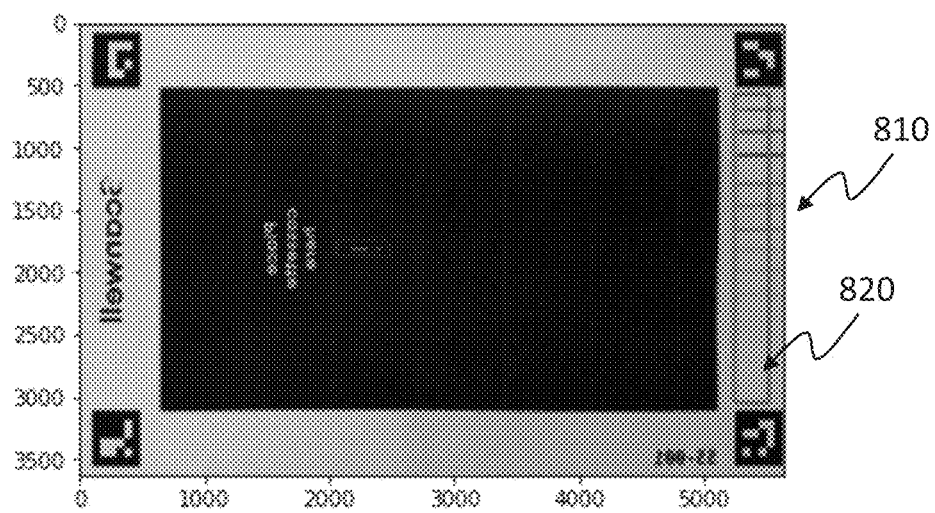
FIGS. 8A and 8B depict example variations of scan surfaces with printed controls, and analysis thereof.
Figure 8A:
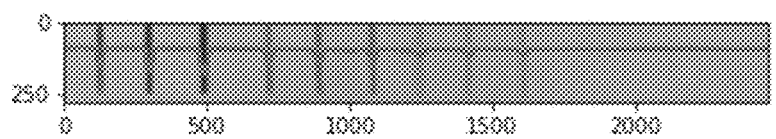

FIG. 8A illustrates an example variation of verifying detection of one or more control markings on a scan surface including a plurality of printed control markings 810. Specifically, FIG. 8A depicts an image of a scan card having control markings 810 that include a set of nine lines of varying reflectivity. The nine lines may be considered representative of test results in a lateral flow immunoassay ranging from faint positive to strong positive. In analyzing the image, a bounded image region 820 may be identified as including the printed control markings 810, based on, for example, identifying fiducials (e.g., ArUco markers) known to be on either side of the appropriate image region 820. The fiducials may be identified with suitable computer vision techniques such as built-in functions of OpenCV and/or similar computer vision software packages. The image region 820 may be cropped, and its pixels may be condensed into a 1D array of pixel values, where each element of the 1D array may include a representative metric (e.g., mean, median, other statistical measure, etc.) of an image segment (e.g., row or column of pixels) in the image region 820. The relative values of the elements of this 1D array may be analyzed to determine a series of peaks, each of which may be considered to potentially correspond with a respective control marking. In some variations, white space in the region of the control markings may be used as a negative control, in that the system should expect no peaks to be detected in the white space. The resulting count of identified peaks may be compared to an accepted predetermined value (e.g., known number of control lines). If the peak count is sufficiently similar to the accepted predetermined values (e.g., are at least accepted threshold values, or fall within a certain range of threshold values), then the camera used to take the image of the control markings and/or the imaging conditions may be considered of sufficient quality. In the example of FIG. 8A, analysis of the 1D array for the image region 820 results in a count of nine peaks, which matches the predetermined, known number of control lines 810 on the scan card. Accordingly, FIG. 8A represents a situation in which the control check has passed based on peaks identified in the image region 820, and subsequent image analysis may proceed.

Figure 8B:
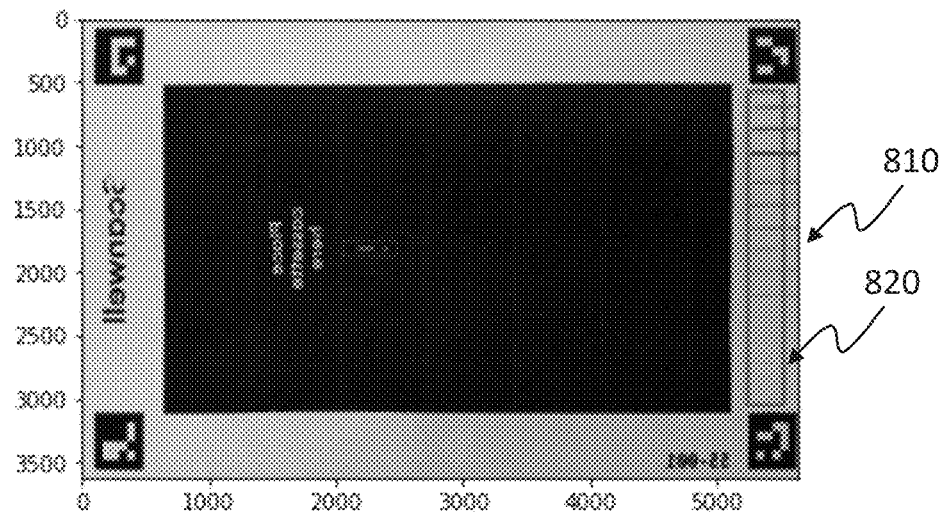
Figure 8B:
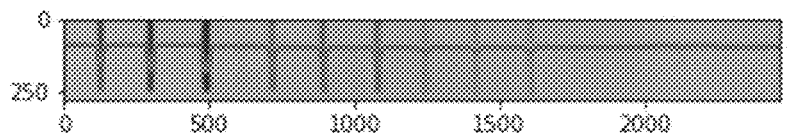

FIG. 8B illustrates another example variation of verifying detection of one or more control markings on a scan surface. The variation of FIG. 8B is similar to that of FIG. 8A, except that the method further considers the prominence of each identified peak, which represents how much the peak stands out due to its intrinsic height and/or location relative to other peaks. The resulting count of peaks and/or their prominences may be compared to accepted predetermined values (e.g., are at least accepted threshold values, or fall within a certain range of threshold values). If the number of peaks and/or their prominences satisfy the predetermined conditions, then the camera used to take the image of the control markings and/or the imaging conditions may be considered of sufficient quality. In the example of FIG. 8B, analysis of the 1D array for the image region 820 results in a count of nine peaks, and measured prominences of each peak also satisfies predetermined conditions. Accordingly, FIG. 8B represents a situation in which the control check has passed based on peaks and prominences identified in the image region 820, and subsequent image analysis may proceed.

Furthermore, in some variations, the printed control markings may additionally or alternatively be assessed with other methods, such as based on detection of each test band contour and measurement of the values within that contour, measurement of the values in pre-determined spatial regions, and/or analysis by a trained machine learning model.

Receiving Images

Figure 6:
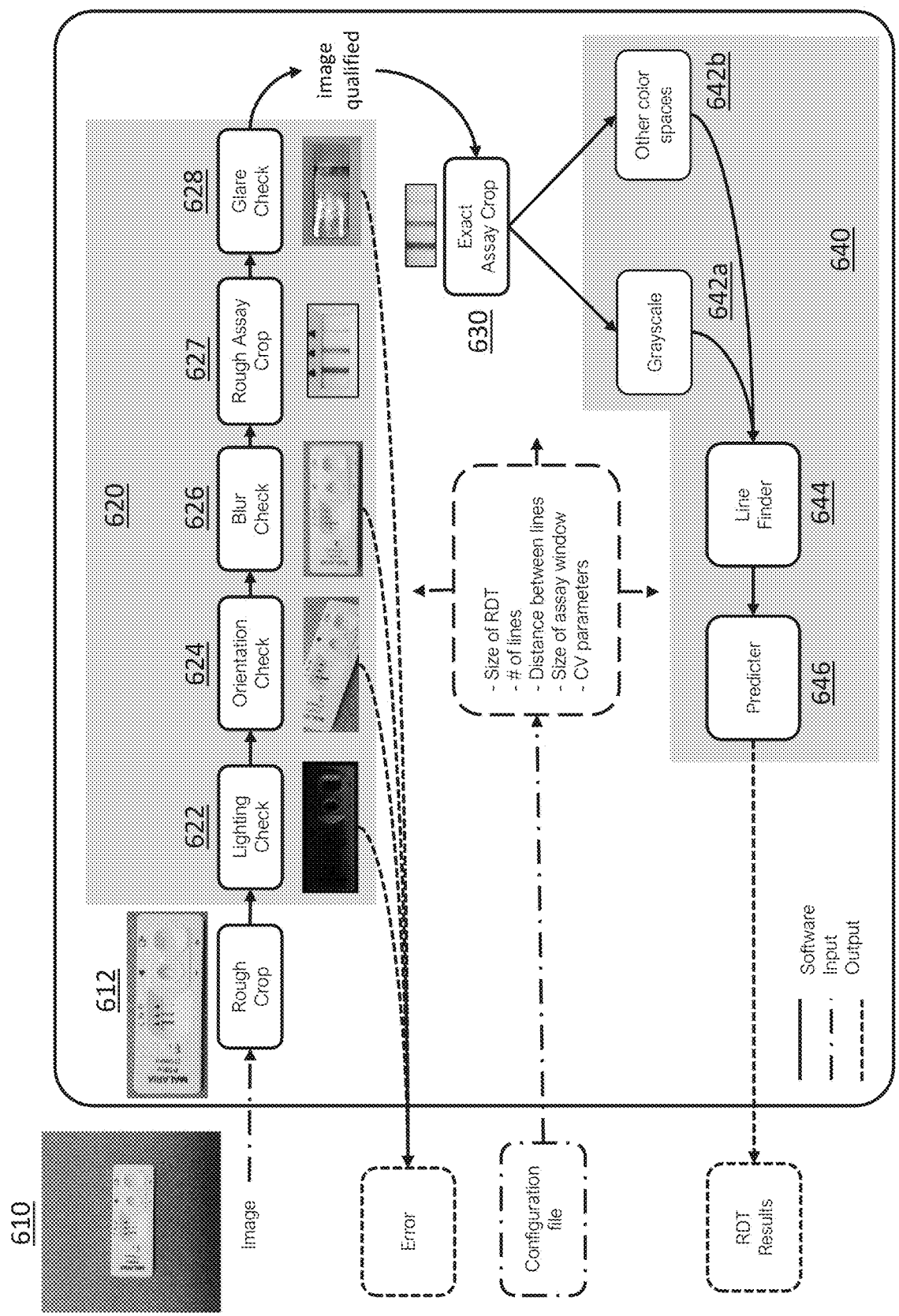
FIG. 6 depicts another flowchart of an example variation of a method for analyzing a diagnostic test.

FIG. 6 illustrates in detail various aspects of computer vision techniques for analyzing an image of a diagnostic test. As described above, an image may be received (610) that depicts a diagnostic test against a background. The background may or may not include a designated scan surface with fiducials. In some variations, the image may be obtained by a user with the assistance of an application executed on a mobile computing device, or by a camera connected to a testing apparatus with a computing device and a display. The application may, for example, display on-screen instructions and/or guidance (e.g., displayed reticle) for the user to obtain a suitable image. In some variations, the application may additionally or alternatively utilize sensors in the computing device or testing apparatus, such as light sensors, to automatically adjust camera settings (e.g., white/color balance, etc.) to optimal conditions and/or provide suggestions to the user (e.g., "Move to somewhere with more light."), and/or close a feedback loop to automatically increase the illumination of the test. The image may be in any suitable format, such as jpeg, png, RAW, etc.

Assuming that the control check (e.g., as described with respect to FIGS. 7A and 7B) has passed, analysis of the image may proceed, such as by generating a roughly cropped version of the image (612) around the imaged diagnostic test to isolate the diagnostic test from the background. In variations in which a control check is not performed, analysis of the received image may automatically proceed as further described below.

Figure 9A:
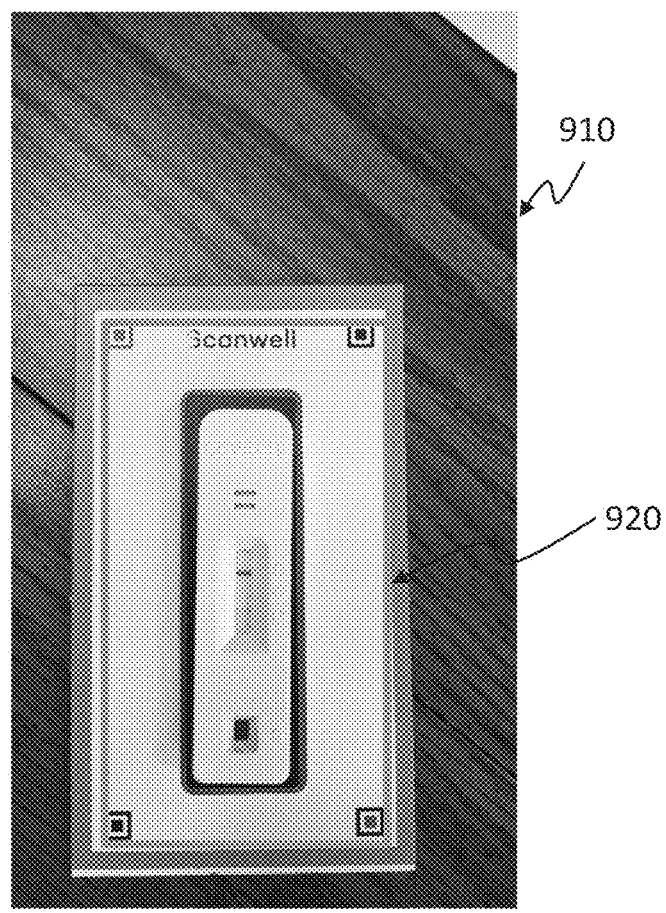
FIGS. 9A and 9B depict example variations of cropping an image to a region of interest including a diagnostic test.

In some variations, the rough crop (612) may be automatically performed using computer vision techniques with the aid of a scan surface. For example, FIG. 9A depicts an image 910 of a diagnostic test on a scan card with spatial markers (QR code markers, though they may include ArUco markers or any suitable fiducial). The image 910 may be roughly cropped to a region of interest 920 that surrounds the diagnostic test. This region of interest 920 may be located, for example, by identifying a set of three or more spatial markers, such as with built-in functions of OpenCV or other suitable computer vision software packages. The area bounded by these spatial markers can be subject to further analysis.

Figure 9B:
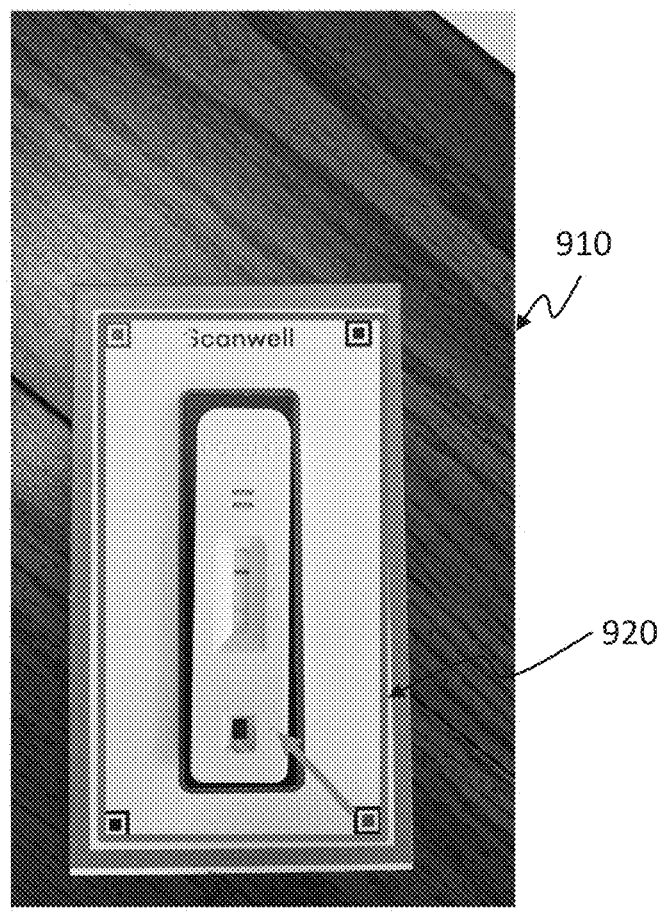

In some variations, the rough crop (612) may be automatically performed using additional computer vision techniques with other image analysis with the aid of a scan surface. For example, FIG. 9B depicts an image 910 of a diagnostic test on a scan card with spatial markers (QR code markers), where the image 910 may be cropped to a region of interest 920 that surrounds the diagnostic test. Like the method described above with respect to FIG. 9A, three of more spatial markers (e.g., QR code markers, though they may include ArUco markers or any suitable fiducial) may be identified, but here the spatial markers may be identified by converting the image 910 to a different color space and identifying contours that indicate the location of each spatial marker. For example, the image may be converted to grayscale to make the analysis color-agnostic, then threshold cutoffs may be applied to help distinguish between the region of interest and the background. The threshold cutoffs may, for example, be based on heuristically-determined threshold that may be a function of average light intensity of target area vs. a "background" area, and contour detection to identify candidate locations of spatial markers. Test of region size and/or region aspect ratio may be applied to candidate locations of spatial markers to identify where the spatial markers are located in the image. In the variation shown in FIG. 9B, one of the spatial markers includes a red square in a predetermined, known location among the spatial markers (lower righthand corner). After the set of spatial markers is located, the red square is identified, and the region of interest 920 is identified as an area of the image 910 that is a multiple of that red square (e.g., a region of (M times the height of the red square)×(N times the width of the red square)), using a corner of the red square or other suitable point relative to the red square as an origin for multiplied coordinates.

Additionally or alternatively, a rough crop of an image may be automatically performed by first converting the image to grayscale and applying threshold cutoffs as described above with respect to FIG. 9B. Subsequently, one or more filters (e.g., median filters) may be used to remove shadows from the image. Open, closed, and/or gradient morphology operations may be performed on the image, and analysis may be focused on regions of the image that were outlined by the on-screen reticle. Min-area algorithms may be used to determine a best-fit box around the diagnostic test as the region of interest for a rough crop of the image.

Furthermore, in some variations, a rough crop (612) of the image of the diagnostic test may additionally or alternatively include manual input to designate boundaries of the diagnostic test. For example, after a user takes an image of the diagnostic test against a background, such as with a mobile computing device (e.g., smartphone) executing a mobile application, the mobile application may prompt a user to indicate a region of interest around the imaged diagnostic test. A user may indicate the region of interest by manually tracing a region of interest on the displayed image using a suitable graphic user interface and/or indicating vertices of a geometrical region of interest (e.g., corners of a rectangle), for example. Alternatively, the user may crop, mark, or otherwise edit the original image of the diagnostic test using any suitable photo editing application on a computing device, and designate that edited photo for further analysis. As yet another example, a rough crop of the image of the diagnostic test may additionally or alternatively be based on an on-screen reticle and/or other suitable guide displayed on a viewing screen of an imaging device. For example, a GUI of an imaging device (e.g., smartphone) may display a reticle having the same aspect ratio as a target (e.g., diagnostic test, test region of the diagnostic test, etc.), where a user may align the target with the reticle prior to capturing the image. As a result, in some variations, the rough crop may be based on a cropped region of pixels in the received image that corresponds to the displayed reticle.

In some variations, a rough crop (612) may incorporate both automatic determination and manual input relating to a region of interest in the image of a diagnostic test. For example, any of the above-described automated techniques may determine a proposed region of interest defining a rough crop around the imaged diagnostic test, and the proposed region of interest may be displayed on a screen of a computing device (e.g., smartphone) for confirmation and/or manual adjustment by a user.

Additionally or alternatively, a rough crop (612) of the image may incorporate known characteristics of the diagnostic test being imaged. For example, the type (e.g., brand, etc.) of the diagnostic test may be determined, and one or more characteristics such as overall shape or aspect ratio of the diagnostic test may be known for that type of diagnostic test (e.g., in a stored configuration file). Information from the configuration file for that diagnostic test may be utilized in verifying appropriate size and/or shape of the region of interest in the image, for example. The type of the diagnostic test may be determined automatically (e.g., optical character recognition of branding on the imaged diagnostic test, other distinctive features, machine learning, template matching, etc.) and/or through manual input on a computing device (e.g., selected by a user from a displayed, prepopulated list of diagnostic tests with known characteristics). In some variations, a proposed diagnostic test type determined through automated methods may then be manually confirmed or corrected by the user. Furthermore, in some variations, such confirmation or correction may be used to further train a machine learning model (or otherwise refine the automated methods described above) to improve its accuracy.

The image (e.g., rough cropped version of the image) may, in some variations, be further pre-processed prior to (or during) image validation such as that described below. For example, pre-processing may include removing shadows from the image. For example, shadows may be removed by transforming the image to grayscale to make the image color-agnostic, measuring the mean light level across each axis of the image and generating a 1D array of light level across each axis, and applying these 1D arrays along each axis of the image in a manner (e.g., division) that darkens the lighter areas and lightens the darker areas.

Validating Images

The roughly cropped version of the image may be analyzed through a series of one or more validation processes to ensure quality of the image (620). One or more various aspects of the image may be validated for quality, including but not limited to lighting level, color balance, exposure level, noise level, image blur level, presence of shadows, and/or presence of glare in the received image. As described in detail below, these aspects may be characterized for validating image quality using various techniques, such as computer vision techniques. In some variations, one or more of these aspects may be characterized for validating image quality using one or more suitable trained machine learning models (e.g., deep learning techniques). For example, a machine learning model may be trained in a supervised manner using training data including images with labeled features (e.g., acceptable or not acceptable orientation of a test, acceptable or not acceptable blur and/or noise level in an image, acceptable or not acceptable level of exposure, lighting, or color balancing, identified spatial coordinates of a crop of the image, isolated test or test region relative to the background, identified orientation of a test, etc.) that may be used to train a neural network or other suitable type of machine learning technique to identify images of suitable quality with respect to certain characteristics. Machine learning models trained in unsupervised or semi-supervised manners may additionally or alternatively be used to validate image quality with respect to one or more aspects of the image.

In some variations, as shown in FIG. 6, validating quality of the image (620) may include performing any one or more of lighting, saturation, color balance, or illumination checks (622) to ensure there is sufficient (or excessive) illumination of the diagnostic test. For example, a lighting check may be performed by computing an average (e.g., mean) red-green-blue (RGB) of the image, and then comparing the average RGB value of the image to a predetermined threshold condition such as a threshold value or range of values. A suitable threshold value or range may, for example, be heuristically determined. If the average RGB value does not satisfy the predetermined threshold condition, then the image may be considered to be of insufficient quality, and an error may be communicated to the user indicating that the image has failed validation processes. It should be understood that in other variations, average values of channels in other color spaces (e.g., YUV, CYMK, etc.) may alternatively be used when performing the lighting check described above. In other variations the V channel of the HSV color space may be used. Additionally, information provided by the camera or other tools (e.g., BV, lux, ISO, ET, focal length) can be used alone or in combination with each other and/or calculated measurements to determine appropriate illumination.

Additionally or alternatively, validating quality of the image may include performing an exposure check to ensure that the image is properly exposed. In some variations this can be performed by reviewing information provided by the camera or other tools (e.g., BV, lux, ISO, ET, focal length). In some variations, this can be performed by identifying expected regions of the image and comparing them with each other to ensure that their relative values are within or outside of a known heuristically determined range or value, or within or outside of a per-image or region computed range or value. In some variations this may include the above items individually or in combination.

Figure 10I:
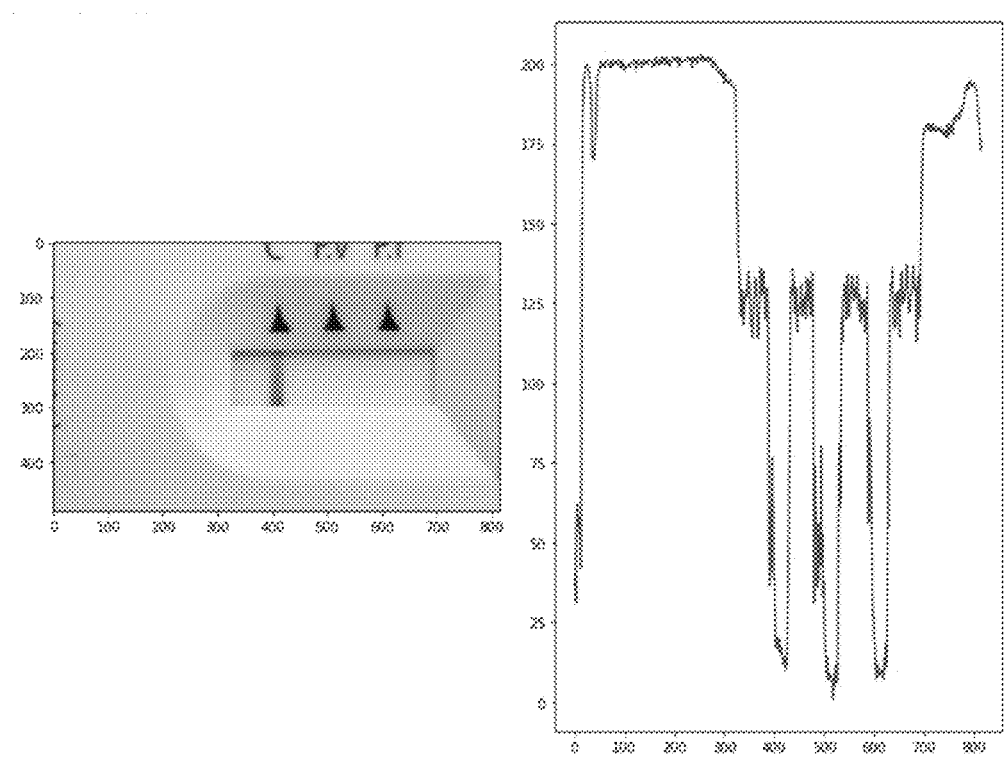

Additionally or alternatively, validating quality of the image (620) may include performing an orientation check (624). In the orientation check, amount of rotation of the diagnostic test within the image may be measured, and orientation of the diagnostic test within the image frame may be corrected accordingly. In some variations, known markings on the diagnostic test may function as a "fingerprint" or informative reference for determining orientation. For example, FIG. 10A depicts an image of a diagnostic test cassette that is rotated within the image frame. Black print arrows on the cassette (e.g., arrows adjacent to the assay window) may provide a helpful reference for determining orientation of the diagnostic test in the image. The image may be converted to another color space or a channel of another color space (e.g., grayscale or LAB L channel, etc.). A 1D array may be created, where each element of the 1D array includes a representative metric (e.g., mean) of pixel values for a region (e.g., column or row) of the image. The 1D array may be filtered (e.g., with a median filter or other appropriate filter) to remove noise and/or other artifacts. The position of peaks in the 1D array (FIG. 10H) may be considered to correspond to the black print markings on the cassette, and may indicate the angle of orientation of the assay within the image (or the flipped 180-degree orientation of the assay, though a non-regular spacing between the black print arrows or other asymmetrical characteristic of the markings may help distinguish between the actual orientation and the flipped 180-degree orientation). Due to high contrast between the white/light cassette material and the black print markings on the cassette, the prominence of these peaks is also expected to be high, which may further help with identification of the orientation of the assay. Based on the determined orientation, a rotational transformation may be applied to the image to align the diagnostic test to the image frame (FIGS. 10E-10G). As a result, the image with corrected cardinal orientation of the diagnostic test may appear to have an expected number of peaks and prominences for the known type of diagnostic test (FIG. 10I).

Example variations of methods for performing an orientation check are shown in FIGS. 10B and 10C. For example, as shown in FIGS. 10B and 10C, the image may be converted to a different color space that augments a feature or set of features that are representative of alignment. One or more computer vision methods or combination of computer vision methods may be used to isolate the alignment representative feature(s) and identify its orientation. For example, suitable computer vision methods for isolating such features and identifying orientation include use of one or more minArea bounding boxes, contour algorithms, etc. As another example, the received image may be cropped (e.g., variations for performing a rough crop of the image as described above), a contour operation may be performed on the resulting image. Images having contours within an expected region may be accepted, while any images with contours outside the expected region may be rejected as poorly oriented. Additionally or alternatively, one or more suitable computer vision techniques may be used to identify the outline of a target image region such as the diagnostic test or feature of the test (e.g., test region), or other targeted predetermined region of the image or test. For example, one or more of edge detection (e.g., Canny, Diriche, Differential, Sobel, Prewitt, Roberts cross, etc.), ridge detection (e.g., Hough transforms, etc.), blob detection (e.g., LoG, DoG, DoH, MSER, PCBR, etc.), feature detection (e.g., affines, SIFT, SURF, GLOH, HOG, etc), and/or deep learning techniques may be used to determine the outline of a target region. Thereafter, any in-plane or out-of-plane rotations may be identified based on the identified region using aspect ratio, area, or perspective transformations, etc. that may calculated or determined in order to measure the degree to which the region is misaligned.

In some variations, an excessively rotated or misaligned image (e.g., rotation of at least a predetermined threshold of degrees), such as that determined by any of the above-described techniques, may lead to a rejection of the image. The user may then be prompted to collect a more properly aligned image. Additionally or alternatively, a transformation may be performed to restore the image to an expected state for further analysis and/or further manual confirmation that the image looks correctly oriented.

In some variations, validating quality of the image (620) may additionally or alternatively include performing a blur or noise check (626) to determine whether the amount of blur or noise in an image is acceptable. For example, such a check may include optionally converting the image into a any one or more of a variety of color spaces and applying one or more computer vision techniques in various suitable combinations. Examples of suitable computer vision techniques for reducing blur include Laplacian variance, Laplacian mean, NIQE, Tenengrad, Sobel functions, Fast Fourier Transform FFT), etc. In some variations, amount of blur or noise may be characterized by generating an image quality metric for the entire image or a region of interest. If this metric is beyond a predetermined threshold, or a dynamically set threshold, or if some combination of these values falls beyond a combination of thresholds, the image is treated as having too much blur and/or noise for subsequent analysis. Other methods may include using saliency maps or trained deep learning models. Additionally or alternatively, a reference may be used, such as by comparing a sharpened version of the image or region with a reference, or a smoothed version of the image or region with a reference, and/or performing intentional blurring on the image or region and comparing to a reference, etc. The reference may include, for example, the original image, a region of the original image, a pre-determined reference image, or a processed image or region of an image. This comparison results in a metric that can then be used as a measurement of the amount of blur or noise in the image.

Additionally or alternatively, in some variations, validating quality of the image (620) may include performing a glare check (628) to determine whether the amount of glare in an image is acceptable. In some variations, the glare check may include converting the image into a any one of a variety of color spaces and then applying a variety of computer vision techniques in various suitable combinations, such as using percentage max values and saliency maps. In some instances, glare may cause saturation of the camera sensor, so values at or near the maximum value reported by the sensor may be treated as glare. For example, on a scale from 0 to 255, any pixel with intensity greater than 240 may be treated as potential glare. Furthermore, any pixel having an intensity that meet a threshold value (dynamically set value or pre-set value) may be treated as glare. The value may be an absolute value, or may be defined relative to a maximum intensity in the image, such as within three counts from the maximum value in the region of interest. Furthermore, in some cases glare manifests as pixels that are far brighter than their surroundings. A second dynamic threshold value, such as the median pixel intensity plus two standard deviations may additionally or alternatively be used for determining whether to treat a pixel as glare. In some variations, an overall glare level for the image may be determined based one or more of these pixel intensity tests. For example, pixels meeting one or both of the above-described criteria may be summed and divided by the total number of pixels in the region of interest, to determine a percentage or fraction of pixels that meet criteria for glare. The fraction of pixels meeting the criteria for glare, divided by the total number of pixels, is reflective of the glare level within the region of interest. Other methods for performing a glare check may additionally or alternatively include processing a converted or non-converted image using a sliding window, and performing a transformation within the window based on features of the window compared to the rest of the image in order to isolate regions of glare.

Figure 11:
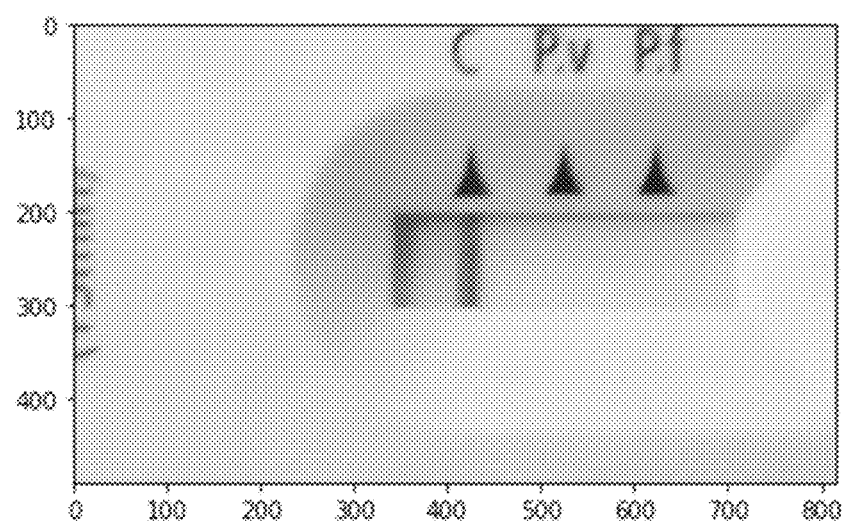
FIG. 11 depicts an example variation of cropping an image to a test region of a diagnostic test.

Glare may be present, for example, on the plastic-covered window of a test region (e.g., assay) of a diagnostic test cassette. Accordingly, in some variations to aid the glare check, a crop of the image to isolate the test region from the rest of the diagnostic test may be performed either manually (e.g., similar to that described above for a rough crop to isolate the diagnostic test from background) and/or in an automated manner. The rough crop (627) may crop out the sample port of the diagnostic test, as well as markings on the cassette (e.g., handwritten ink marks, etc.). As an example of an automated manner of performing a rough crop of the image to isolate the test region, FIG. 11 illustrates a variation of performing a rough crop of the image depicting a diagnostic test including a test strip in a cassette. In some variations, assuming that the test strip is somewhat centered within an on-screen reticle displayed on a camera device (e.g., on a mobile computing device), the rough crop may remove a predetermined portion (e.g., percentage) of the image perimeter. For example, the rough crop may remove an outer 30% of the image perimeter, though the percentage to be cropped may be any suitable value.

Additionally or alternatively, the test region may be located using an outline-based technique. For example, the test region may be located based at least in part on an identified outline of the diagnostic test and estimating location of the test region relative to the outline of the diagnostic test. For example, computer vision techniques may identify an outline of the diagnostic test (e.g., cassette) using thresholding, edge finding, blob finding, contour detection, etc. The location of the test region may be determined based on predetermined coordinates relative to the outline of the diagnostic test and/or other markers, thereby using such known markers in the image as spatial landmarks. The predetermined coordinates may, for example, be known after determining the type of diagnostic test (which may be determined automatically and/or manually as described above).

In some variations, a crop of the image to isolate the test region from the rest of the image may be performed prior to any of the image validation tests. Furthermore, it should be understood that while FIG. 6 depicts image validation processes to be performed in a certain order, the processes such as lighting check (622), orientation check (624), blur/noise check (626), and glare check (628) may be performed in any suitable order, with any check being omitted or additional checks being inserted, as tailored based on the determined needs of the test.

Furthermore, in some variations, validation of the image (620) may utilize information from a configuration file that associated with the type of diagnostic test being imaged. The type of diagnostic test may be determined automatically and/or manually (e.g., as described above) and an associated configuration file may be accessed. Information such as the size or aspect ratio of the diagnostic test, the number of lines in the test region, distance between the lines in the test region, the location of the test region compared to other landmarks in the test (e.g. top left corner), size of test region (e.g., assay window), etc. may be used to help verify whether the diagnostic test is adequately imaged. The configuration file may also contain information such as thresholds, or algorithm controls regarding how and which quality techniques are employed and how such techniques are employed.

Additionally, any one or more of the above validation processes may be customized and/or otherwise tailored for the device(s) performing such processes. Knowledge of device descriptors such as make, model, camera focal length, and/or other identifying characteristics of the imaging device (e.g., smartphone) may be obtained from the operating system, or from values predetermined for a custom software build for a specific device, etc. The customization of one or more validation processes may be based at least in part on such device-specific descriptors, and stored as predetermined instructions. The predetermined instructions may be included in the code for the algorithm, or could be downloaded from a remote location (e.g., server, remote memory device(s), cloud storage, etc.).

Locating Test Region

The test region (e.g., assay window) may be located to proceed with diagnostic test analysis. The test region may be located in various suitable manners. For example, the rough test region isolation techniques described above (e.g., with reference to FIG. 11, and/or an outline-based technique) may be sufficiently precise in some instances to proceed with analysis. Alternatively, in some variations, as shown in FIG. 6, after an image has been validated to be of sufficient quality, a more precise or exact crop of the image may be performed (630) to more precisely isolate the test region (e.g., assay window) of the diagnostic test. In some variations, as described in detail below, suitable computer vision techniques may be used to locate and/or isolate the test region in the image. Additionally or alternatively, the test region may be isolated and/or located using one or more suitable trained machine learning models (e.g., deep learning techniques). For example, a machine learning model may be trained in a supervised manner using training data including images with labeled test region portions (e.g., assay window, reagent pad, etc.) that may be used to train a neural network or other suitable type of machine learning technique to identify and/or isolate the test region in an image. Machine learning models trained in unsupervised or semi-supervised manners may additionally or alternatively be used to locate and/or isolate the test region in an image.

Figure 12A:
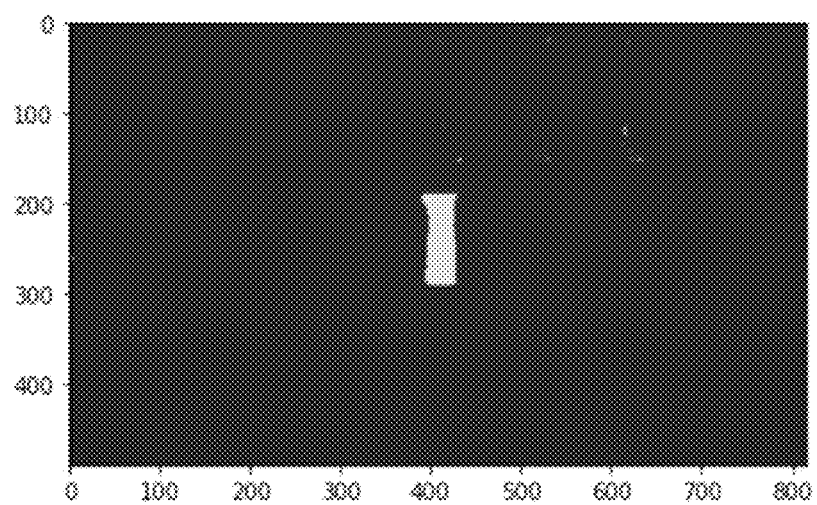
FIGS. 12A and 12B depict an example variation of cropping an image to a test region of a diagnostic test.
Figure 12B:
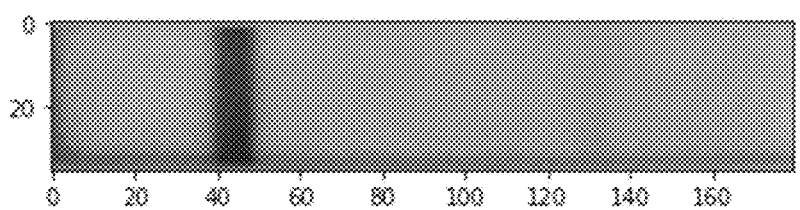

For example, in some variations, the test region may be located based at least in part on a color-based method. By way of illustration, as shown in FIG. 12A, the cropped image (e.g., rough crop of the test region) may be converted to the LAB color space or another suitable color space. The image array may be split into L, A, and B channel 2D arrays, and a high percentile value (e.g., 99th, 98th, 97th percentile, etc.) in the highest contrast channel for the diagnostic test may be calculated among the 2D arrays. The highest contrast channel may be selected based on the color of the diagnostic test. For example, a high percentile value of the A channel array may be determined for a lateral flow immunoassay test with red/pink lines. Any portions of the image that is not in the predefined percentile A channel value may be removed via a binary or Otsu filter or the like. In other words, the binary or Otsu filter may effectively threshold out all but the brightest A channel values (e.g., brightest 1%, 2%, 3%, etc. in the A channel) from the image. The largest contour may be identified in the remaining image, and this contour may be considered the control line in the test region. As shown in FIG. 12B, the location (e.g., bounds) of the test region may be extrapolated based on the estimated location of the control line, and/or any other information such as an estimated aspect ratio of the test region (either nominal value or known from a configuration file associated with the diagnostic test, etc.). Other high contrast channels may be used depending on the color of the test (e.g., B channel for a diagnostic test that produces blue lines).

Furthermore, the color-based method of locating the test region may utilize any suitable color space. In some variations, the cropped image may be converted to the YUV, XYZ, HSV, CYMK, or other suitable color space and the highest contrast color channel in the selected color space may be used as described above to identify the control line for test region extrapolation. For example, the cropped image may be converted to the YUV color space, and for a diagnostic test with red/pink lines, the V channel may be used to threshold out portions of the image and identify the control line for test region extrapolation.

As another example, the cropped image may be converted to a grayscale image, and the grayscale image may be converted to a 1D array, where the elements of the array are a representative metric (e.g., mean) of a portion such as a row or column of the grayscale image. Peaks may be identified in the 1D array, and peak(s) with the highest prominence may be considered the control line as a basis for extrapolation for the entire test region. In the event that more than one high intensity line or peak are present on the test strip, the peak that is closest to the expected position of the spatial landmark control line may be determined to be the spatial landmark. In some instances, multiple control lines may be present and each control line may be used as a spatial landmark to refine the location of the test area.

In some instances, the exact test region (e.g., assay window) may be partially obscured by shadow due to environmental conditions (e.g., lighting conditions), which may make it more difficult to precisely locate the test region. For example, in some instances, light illuminating the diagnostic test from a low angle (e.g., through a floor to ceiling window) may cause the test cassette to cast a shadow onto at least a portion of the test region. In such instances, a heavy shadow may be cast onto a first portion of the test region while a second portion (e.g., remainder) of the test region may be well-illuminated. Accordingly, most of the test region may be found by thresholding (e.g., binary thresholding, such as that described above) to show only the brightest areas; however, the darkened or shadowed portion of the test region is more difficult to find through solely binary thresholding). Thus, in some variations a technique analyzing Laplacian values may provide an improved, more accurate method of identifying the test region in an image, by leveraging the understanding that image regions with a high Laplacian value indicate edges of the dark regions of the test region. Accordingly, adding the "bright" and "dark" areas of the test strip may result in a combined image that is likely to include the entire test region.

For example, in some variations, a method for identifying a test region in an image may include determining one or more high-Laplacian regions of the image that have Laplacian values above a predetermined Laplacian threshold, determining one or more bright regions of the image that have a brightness above a predetermined brightness threshold, combining the one or more high-Laplacian regions and one or more bright regions of the image through a bitwise "OR" operation, and defining the test region based on the contour of the combined high-Laplacian and bright regions of the image.

In an exemplary variation of this method, the image may first be converted to grayscale. The Laplacian of the grayscale image may be calculated, and a suitable binary Laplacian threshold may be applied to the Laplacian to form a thresholded Laplacian image that includes image portion(s) having Laplacian values above the Laplacian threshold. The Laplacian threshold may, for example, be the average (e.g., mean) Laplacian value of the Laplacian image plus the standard deviation in Laplacian image of the Laplacian image. A set of further erosions and dilations may then be applied to the thresholded Laplacian image to smooth the test region contour. Furthermore, a suitable binary grayscale threshold may be applied to the grayscale image to form a thresholded grayscale image that includes image portion(s) having brighter grayscale values above the grayscale threshold. For example, the grayscale threshold may be the average (e.g., mean) grayscale value of the grayscale image plus the standard grayscale deviation of the grayscale image. Another set of further erosions and dilations may then be applied to the thresholded grayscale image to smooth the test strip contour. The thresholded Laplacian image and the thresholded grayscale image may then merged with a bitwise "OR" operation. An additional set of further erosions and dilations may then be applied to the merged image to smooth the test region contour. This merged image may then passed to a contour finding function. If a contour with the expected (e.g., correct) size, aspect ratio, and position are found, this contour is then marked as the test region contour and further analysis of the test region may proceed as described elsewhere herein.

In another exemplary variation, the received image may be converted in two manners to form a grayscale version of the image, as well as another version of the image in a suitable color space such as the HSV color space. Similar to the example above, the Laplacian of the grayscale image may be calculated, and a suitable binary Laplacian threshold may be applied to the Laplacian to form a thresholded Laplacian image that includes image portion(s) having Laplacian values above the Laplacian threshold. The Laplacian threshold may, for example, be the average (e.g., mean) Laplacian value of the Laplacian image plus the standard deviation in Laplacian image of the Laplacian image. A set of further erosions and dilations may then be applied to the thresholded Laplacian image to smooth the test region contour. In this example, the V, or value, channel of the HSV color space may be used for thresholding to identify bright regions of the image. For example, a "FOR" loop may be used to iteratively call a thresholding function, where in each cycle of this loop, a different cutoff value may be used and a binary threshold is applied at the cutoff value to form a thresholded value (V) image. A set of further erosions and dilations may then be applied to smooth the test strip contour. The thresholded Laplacian image and thresholded value (V) image may then be merged with a bitwise "OR" operation. A set of further erosions and dilations may then be applied to smooth the test region contour. This merged image may then passed to a contour finding function. If a contour with the expected (e.g., correct) size, aspect ratio, and position are found, this contour is then marked as the test region contour and further analysis of the test region may proceed as described elsewhere herein.

In some variations, a diagnostic test may include only one test region (e.g., one assay window), and only one such test region may need to be located in the image for analysis. However, in some variations, a diagnostic test may include multiple test regions (e.g., multiple assay windows, or multiple test regions distributed across a single assay window), and accordingly in these variations multiple test regions may be located by repeating the processes described above as appropriate.

In some variations, the test region may additionally or alternatively be isolated by using any number, order, or combination of suitable computer vision techniques that isolate the outline of the test region (e.g., thresholding, edge finding, blob finding, contour detection, etc. and/or other techniques described above). In some variations, a technique for isolating the test region can be aided by first isolating the diagnostic test in the image (e.g., using techniques described previously) to create a subset region representing the diagnostic test, and then, using known features of the test (e.g., which may be determined from a configuration file as described above), and identifying a subset region in which to search for the test region.

Predicting Test Result

Given a sufficiently cropped image that adequately isolates the test region(s) of the diagnostic test in the image, a test result may be predicted (640) based on analyzing the test region depicted in the image. As shown in FIG. 6, the precise or exact cropped image may be converted to grayscale (642*a*) or a suitable high contrast color space (642*b*), or may be converted to multiple versions including grayscale and color space versions for further analysis. Furthermore, test lines in the test region may be more easily differentiated from shadows in ratiometric color channels such as the LAB "A" or LAB "B" or YUV "V" channels, which are resistant to interference from shadows. Accordingly, in some variations, when determining the position of a line in the test region (644), the use of these channels may be preferable to the use of a channel that combines a measure of luminance and color.

In some variations, the cropped test region image may be processed prior to further analysis, in order to remove problematic regions (e.g., rows) that may be misleadingly dark due to dirt, foreign bodies, shadows, etc. For example, the darkest rows of pixels (e.g., as determined in a grayscale version of the image) may be thresholded out based on a threshold cutoff determined by highest percentile value (e.g., 99%, 98%, etc.) in the image or a portion thereof (e.g., by row), based on determining peak values of pixel intensity across rows, and/or in any suitable manner.

FIGS. 13A-13F are schematic illustrations of aspects of an example variation of predicting a test result from the imaged test strip. For example, starting with a sufficiently cropped image that isolates the test region of the diagnostic test in the image (FIG. 13A), the image may be converted into any suitable high contrast color space such as LAB or YUV, etc. (FIG. 13B). The converted image may be split into multiple color channels (FIG. 13C). For example, an image in the LAB color space may be split into L, A, and B channels. A representative or descriptive statistic (e.g., mean) may be determined for each column of the high contrast channel (e.g., A for a diagnostic test with red/pink lines) and condensed into a 1D array (FIG. 13D). The peaks in this 1D array may be located (FIG. 13E) and identified as potential lines in the diagnostic test, as every line on the test strip should yield one peak in the 1D array.

If analyzing the image in grayscale, the grayscale image may be condensed into a 1D array similar to that described above, where the elements of the array are a representative metric (e.g., mean) of a portion such as a row or column of the grayscale image. Similarly, the peaks in this 1D array may be located and identified as potential lines in the diagnostic test.

Generally, in both color space and grayscale image analysis, the relative position of each peak may be determined, as well as the prominence of each peak. In some variations, the determination of the presence of a line may be based on any one or more of peak prominence, peak position (e.g., relative to other peaks and/or borders of the test region), and peak width. In some variations, a control line may be identified first (e.g., as the strongest presence of a line, based on position of a peak relative to a test region border, etc.), before searching for other peaks/lines that may represent the test result line. If no peaks are found, then the test may be treated as invalid. Similarly, if no control line is found, the test may be treated as invalid.

As an illustrative example, the identified peaks may be analyzed under a set of rules as shown in Table 1, in a repeated loop manner (e.g., in a "for" loop for all peaks). Expected positions of control lines and/or test lines, and/or threshold for these lines, may be based on information from a configuration file associated with the type of diagnostic test being imaged. Alternatively, such positions may be otherwise predetermined, such as with nominal positional values.

In the table below, the noted threshold variables have relative values as follows:

[very_low_threshold]<[slightly_lower_threshold]<
 [relatively_low_threshold]

TABLE 1

Analysis of peaks in image for prediction of diagnostic test result

| Rule # | Rule description |
|---|---|
| 1 | If no peak has a prominence greater than [relatively_low_threshold] => image is invalid. |
| 2 | If median LAB or RGB (or other color space) values are outside of an accepted range => image is invalid. |
| 3 | If peak is in a correct position and has a prominence above a position-specific threshold => the peak is added to a list of detected lines. |
| 4 | If peak is in a position where a control line is expected, and no control line has been detected, and peak has a threshold above a predefined threshold or a dynamic threshold that scales with image characteristics such as light level => treat this as the control line. |
| 5 | If peak is in a position where a strong test line is expected, and a control line has been detected, and peak has a threshold above [slightly_lower_threshold] => treat this as a test line. |
| 6 | If peak is in a position where a faint test line is expected, and a control line has been detected, and peak has a threshold above a predefined threshold or a dynamic threshold that scales with image characteristics such as light level => treat this as a test line. |

Additionally or alternatively, once the exact location of the test region is determined (e.g., via any of the techniques described above), intensities of lines in the test region can be measured at expected positions in the test region (e.g., known line locations within the assay window for that particular kind of diagnostic test). These line intensities may be measured in a range of positions in accordance with the manufacturing tolerances of the test strip for the diagnostic test. For example, if a known manufacturing tolerance for test line location has a range of 1 mm (e.g., ±0.5 mm relative to a nominal test line position, or ranging between 0.5 mm to the left of the nominal test line position and 0.5 mm to the right of the nominal test line position), then line intensity measurements for that test line may be performed at image locations within that same 1 mm spatial range in the test region. In some variations, the maximum intensity in that 1 mm spatial range region may be used as the representative line intensity for purposes of analyzing test result. However, other representative values (e.g., mean line intensity value, average of top quartile of line intensity values, etc.) may be used for purposes of analyzing test result. Furthermore, it should be understood that a manufacturing tolerance of 1 mm is only an example for illustrative purposes, and the specific appropriate value may vary among test type, diagnostic test brands, etc.

Additionally or alternatively, the test region portion of the image may be analyzed to predict a test result (646) using one or more suitable trained machine learning models (e.g., deep learning techniques). For example, a machine learning model may be trained in a supervised manner using training data including images with labeled test results (e.g., faint positive, moderately strong positive, strong positive, etc.) for various kinds of diagnostic tests. This training data may be used to train a neural network or other suitable type of machine learning technique to predict a test result from the image. Machine learning models trained in unsupervised or semi-supervised manners may additionally or alternatively be used to predict a test result from the image.

While the methods are primarily described above with reference to analyzing lateral flow immunoassay tests, it should be understood that aspects of the methods may also apply to other kinds of diagnostic tests (e.g., colorimetric immunoassay tests). For example, in some variations, analysis of colorimetric immunoassay tests may include identifying a test region (e.g., using fiducials on a scan surface). However, instead of involving locating control lines and/or test lines, predicting a test result for a colorimetric test may include locating control vessels and/or test vessels, and comparing a detected color of a sample in the test vessel(s) with one or more predetermined colors (e.g., color reference array) to assess the diagnostic test result. In some variations, the color-based image analysis may be similar to that described in U.S. Pat. Nos. 8,655,009 and 8,911,679, each of which is incorporated above.

Furthermore, in some variations for analyzing colorimetric tests, a test region (e.g., reagent pad) may be located by finding its contours such as with a suitable contour algorithm. Once the test region is located in the image, the portion of the image depicting the test region may be converted to a color space that is best suited for analysis of its color. For example, in many cases, the LAB, YUV or CIE-XYZ color spaces are best for analysis of reagent pad color. Once the test region image portion has been isolated and converted to an appropriate color space, descriptive statistics about its color may be measured. For example, the median value a descriptive statistic (e.g., value in a color channel in the color space) of the test region image portion is measured. In some variations, any areas where glare or foreign objects are detected on the test region may be disregarded before this calculation of the descriptive statistic is made. Such glare and/or foreign objects may be detected as described above, for example.

In some variations present in the scene of any colorimetric test image may be reference colors, such as in reference color blocks or other icons printed on a scan surface and depicted in the image). These reference color blocks may be located by finding their contours. Once the reference color blocks have been located, images of those color blocks may be converted to a color space that is best suited for the analysis of their color. Descriptive statistics representing the color blocks may be calculated similar to that as described above. These descriptive statistics may be used to generate a color correction matrix, which can be applied to the entire image or just the region of interest. This color correction matrix serves to lessen the impact of unusual illuminant conditions on measurement of the reagent pad color.

In some variations, the color value of the reagent pad may then be translated into a reagent concentration and corresponding test result, such as with a lookup table or equation, which may be stored in memory and accessed at appropriate times.

Communicating the Test Result

After test result(s) have been predicted, they may be output or otherwise communicated to a suitable entity. For example, in some variations the test result may be communicated to the user through a mobile application associated with the diagnostic platform, through a notification message, through email, or in any suitable manner. Additionally or alternatively, the diagnostic test results may be communicated to a medical care team for the user, such as through an associated dashboard or other suitable system in communication with the diagnostic platform. Furthermore, in some variations the diagnostic test results may be communicated to a suitable electronic health record for the user or other memory storage device.

The diagnostic platform may, in some variations, assist in one or more various follow-up actions in view of the predicted test result. For example, the diagnostic platform may help the user become connected with a suitable medical care practitioner to discuss questions or options for proceeding with medical care. The diagnostic platform may suggest and/or facilitate an in-person visit with a medical care practitioner in appropriate. Additionally or alternatively, the diagnostic platform may assist in providing prescriptions for appropriate medications, provide general medical guidance and/or links to resources, and/or other suitable actions to further the medical care of the user in view of the diagnostic test results.

Example Embodiments

Embodiment 1. A method for analyzing a diagnostic test, the method comprising:
  at one or more processors:
  receiving an image depicting a diagnostic test, wherein the diagnostic test comprises a test region indicating a test result;
  validating quality of the image;
  locating a test region image portion of the image depicting the test region of the diagnostic test; and
  predicting the test result based on the test region image portion.

Embodiment 2. The method of embodiment 1, wherein validating quality of the image comprises assessing at least one of lighting level, color balance, noise level, image blur level, presence of shadows, and presence of glare in the received image.

Embodiment 3. The method of embodiment 1, wherein validating quality of the image comprises assessing at least one of location and orientation of the diagnostic test in the received image.

Embodiment 4. The method of embodiment 1, wherein validating quality of the image comprises validating imaged quality of one or more control markings in the received image.

Embodiment 5. The method of embodiment 4, wherein the one or more control markings comprise a plurality of lines.

Embodiment 6. The method of embodiment 4, wherein the one or more control markings comprise a plurality of colors.

Embodiment 7. The method of embodiment 1, wherein locating the test region image portion comprises identifying a boundary of the diagnostic test in the image.

Embodiment 8. The method of embodiment 7, wherein identifying the boundary of the diagnostic test in the image comprises identifying the boundary of the diagnostic test against a high contrast background.

Embodiment 9. The method of embodiment 7, wherein locating the test region image portion comprises locating the test region image portion based at least in part on one or more predetermined test region coordinates relative to the boundary of the diagnostic test in the image.

Embodiment 10. The method of embodiment 9, wherein the one or more predetermined test region coordinates is associated with a type of the diagnostic test.

Embodiment 11. The method of embodiment 1, wherein locating the test region image portion comprises identifying one or more fiducials on a scan surface in the image and locating the test region image portion based on the location of the one or more fiducials.

Embodiment 12. The method of embodiment 1, wherein locating the test region image portion comprises identifying an image portion of interest having a peak representative value of a predetermined color channel in the image, and locating the test region image portion based on the location of the largest contour in the predetermined color channel in the image portion of interest.

Embodiment 13. The method of embodiment 11, wherein the predetermined color channel is in a color space selected from the group consisting of LAB, YUV, HSV, XYZ, and CYMK.

Embodiment 14. The method of embodiment 1, wherein predicting the test result comprises identifying one or more peak prominences in a predetermined color channel in the test region image portion.

Embodiment 15. The method of embodiment 14, wherein predicting the test result comprises evaluating the one or more peak prominences for at least one of a control and a result indicator in the test region image portion.

Embodiment 16. The method of embodiment 1, further comprising receiving one or more images of a user and verifying sample collection by the user based on the one or more images of the user.

Embodiment 17. The method of embodiment 1, further comprising identifying a type of the diagnostic test depicted in the received image.

Embodiment 18. The method of embodiment 1, further comprising communicating the predicted test result to a user.

Embodiment 19. The method of embodiment 1, wherein the diagnostic test comprises a lateral flow immunoassay test.

Embodiment 20. The method of embodiment 19, wherein the lateral flow immunoassay test is a direct flow immunoassay test.

Embodiment 21. The method of embodiment 1, wherein the diagnostic test comprises a colorimetric immunoassay test.

Embodiment 22. The method of embodiment 21, wherein the colorimetric immunoassay test is an isothermal amplification test.

Embodiment 23. A method for facilitating analysis of a diagnostic test, the method comprising:
  at one or more processors:
  receiving one or more images depicting one or more control markings on a scan surface, wherein the one or more control markings are representative of one or more predetermined test results for the diagnostic test; and
  verifying detection of the one or more control markings in the one or more images using at least one computer vision technique.

Embodiment 24. The method of embodiment 23, wherein at least one of the images depicts the diagnostic test and the one or more control markings.

Embodiment 25. The method of embodiment 23, further comprising separately receiving one or more images depicting the diagnostic test.

Embodiment 26. The method of embodiment 23, wherein verifying detection of the one or more control markings in the one or more images comprises generating an array of a representative value of a series of pixels associated with the one or more control markings, determining peaks and/or prominences in the array, and comparing the peaks and/or prominences to one or more predetermined threshold values.

Embodiment 27. The method of embodiment 26, wherein verifying detection of the one or more control markings comprises treating white space in the one or more images as a negative control.

Embodiment 28. The method of embodiment 23, further comprising predicting a test result of the diagnostic test based on an image of the diagnostic test, in response to detecting the one or more control markings in the one or more images depicting one or more control markings.

Embodiment 29. The method of embodiment 23, further comprising notifying a user in response to failing to detect the one or more control markings in the one or more images depicting one or more control markings.

Embodiment 30. The method of embodiment 23, wherein the diagnostic test comprises a lateral flow immunoassay test, and the one or more control markings comprises one or more lines.

Embodiment 31. The method of embodiment 30, wherein the one or more lines vary in at least one of thickness, color, hue, and reflectivity.

Embodiment 32. The method of embodiment 30, wherein the one or more lines includes black and/or gray lines.

Embodiment 33. The method of embodiment 23, wherein the diagnostic test comprises a colorimetric immunoassay test, and the one or more control markings comprises one or more colors.

Embodiment 34. The method of embodiment 23, wherein the scan surface further comprises a test placement guide proximate the one or more control markings, wherein the test placement guide is configured to guide placement of the diagnostic test.

Embodiment 35. A system for facilitating analysis of a diagnostic test, the system comprising: a scan surface comprising one or more control markings, wherein the one or more control markings are representative of one or more predetermined test results for the diagnostic test.

Embodiment 36. The system of embodiment 35, wherein the scan surface further comprises a test placement guide indicating placement of the diagnostic test.

Embodiment 37. The system of embodiment 36, wherein the test placement guide has a color that contrasts with the diagnostic test.

Embodiment 38. The system of embodiment 36, wherein the test placement guide indicates an outline of the diagnostic test.

Embodiment 39. The system of embodiment 35, wherein the diagnostic test comprises a lateral flow immunoassay test, and the one or more control markings comprises one or more lines.

Embodiment 40. The system of embodiment 39, wherein the one or more lines vary in at least one of thickness, color, hue, and reflectivity.

Embodiment 41. The system of embodiment 39, wherein the one or more lines includes black and/or gray lines.

Embodiment 42. The system of embodiment 35, wherein the diagnostic test comprises a colorimetric immunoassay test, and the one or more control markings comprises one or more colors.

Embodiment 43. The system of embodiment 35, wherein the scan surface further comprises at least one spatial fiducial.

Embodiment 44. The system of embodiment 35, wherein the scan surface comprises at least one computer-readable code with identification information.

Embodiment 45. The system of embodiment 35, wherein the one or more control markings are printed on the scan surface.

Embodiment 46. The system of embodiment 45, wherein the one or more control markings are printed with ink or toner.

Embodiment 47. The system of embodiment 46, wherein the one or more control markings are printed with fluorescent ink.

Embodiment 48. The system of embodiment 47, wherein the fluorescent ink comprises at least one selected from the group consisting of: europium, rhodamine, fluorescein, alexa fluor, quantum dots, and fluorescent nanoparticles.

Embodiment 49. A diagnostic test kit, comprising:
a diagnostic test comprising a test region for indicating a test result; and
a scan surface comprising one or more control markings, wherein the one or more control markings are representative of one or more predetermined test results for the diagnostic test.

Embodiment 50. The diagnostic test kit of embodiment 49, wherein the diagnostic test comprises a lateral flow immunoassay test, and the one or more control markings comprises one or more lines.

Embodiment 51. The diagnostic test kit of embodiment 50, wherein the one or more lines vary in thickness.

Embodiment 52. The diagnostic test kit of embodiment 50, wherein the one or more lines vary in color.

Embodiment 53. The diagnostic test kit of embodiment 50, wherein the one or more lines vary in hue.

Embodiment 54. The diagnostic test kid of embodiment 50, wherein the one or more lines vary in reflectivity.

Embodiment 55. The diagnostic test kit of embodiment 50, wherein the one or more lines are black and/or gray.

Embodiment 56. The diagnostic test kit of embodiment 50, wherein the one or more lines are a color that matches an expected color of a test result line in the diagnostic test.

Embodiment 57. The diagnostic test kit of embodiment 49, wherein the diagnostic test comprises a colorimetric immunoassay test, and the one or more control markings comprises a plurality of colors.

Embodiment 58. The diagnostic test kit of embodiment 49, wherein the one or more control markings are printed on the scan surface.

Embodiment 59. The diagnostic test kit of embodiment 58, wherein the one or more control markings are printed with ink or toner.

Embodiment 60. The diagnostic test kit of embodiment 59, wherein the one or more control markings are printed with fluorescent ink.

Embodiment 61. The diagnostic test kit of embodiment 60, wherein the fluorescent ink comprises at least one selected from the group consisting of: europium, rhodamine, fluorescein, alexa fluor, quantum dots, and fluorescent nanoparticles.

Embodiment 62. The diagnostic test kit of embodiment 49, wherein the scan surface further comprises a test placement guide proximate to the one or more control markings, wherein the test placement guide is configured to guide placement of the diagnostic test.

Embodiment 63. The diagnostic test kit of embodiment 49, wherein the scan surface is a first scan surface, and wherein the diagnostic test kit further comprises a second scan surface separate from the first scan surface and comprising a test placement guide.

Embodiment 64. The diagnostic test kit of embodiment 49, further comprising a heating device.

Embodiment 65. The diagnostic test kit of embodiment 64, further comprising a housing comprising the heating device and a test placement guide proximate the heating device, wherein the test placement guide is configured to guide placement of the diagnostic test.

Embodiment 66. The diagnostic test kit of embodiment 65, wherein the scan surface is arranged on the housing.

Embodiment 67. The diagnostic test kit of embodiment 66, wherein the housing is configured to receive a test sample.

Embodiment 68. The diagnostic test kit of embodiment 67, wherein the housing comprises a receptacle configured to receive a test sample vessel.

Embodiment 69. The diagnostic test kit of embodiment 68, wherein the receptacle is proximate the heating device.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A method for facilitating analysis of a diagnostic test, the method comprising:
   at one or more processors of a mobile computing device having at least one image sensor and a display:
   receiving an image captured at the at least one image sensor, the image depicting the diagnostic test, one or more static control markings on a scan surface, and a plurality of image region markers on the scan surface defining a boundary of an image region including the diagnostic test and the one or more static control markings, wherein the one or more static control markings comprise a control marking corresponding to a lower limit of optical detectability for analysis of the diagnostic test;
   prior to analyzing the diagnostic test, assessing an adequacy of at least one of lighting, orientation, and focus conditions associated with the image by verifying detection of the one or more static control markings in the image using at least one computer vision technique, wherein verifying detection of the one or more static control markings comprises:
   determining pixel values for multiple linear series of image pixels in the image,
   generating a 1D array of metrics, each metric in the 1D array of metrics comprising a value calculated based on the pixel values of an individual one of the multiple linear series of image pixels, and
   identifying one or more peaks in the 1D array of metrics; and
   when the one or more processors determine that the at least one of lighting, orientation, and focus conditions is adequate based on the identified one or more peaks in the 1D array of metrics:
   automatically analyzing the diagnostic test based on at least one computer vision technique to determine at least one test result; and
   causing the display to display the at least one test result.

2. The method of claim 1, wherein the image depicts the diagnostic test and the one or more static control markings.

3. The method of claim 1, wherein identifying one or more peaks comprises determining peaks and/or prominences of peaks in the array, and comparing the peaks and/or prominences to one or more predetermined threshold values.

4. The method of claim 1, wherein verifying detection of the one or more static control markings comprises treating white space in the image as a negative control space where no control marking is expected.

5. The method of claim 1, wherein automatically analyzing the diagnostic test comprises predicting a test result of the diagnostic test based on an image of the diagnostic test, in response to detecting the one or more static control markings in the image depicting one or more static control markings.

6. The method of claim 1, wherein the diagnostic test comprises a lateral flow immunoassay test, and the one or more static control markings comprises one or more lines.

7. The method of claim 6, wherein the one or more lines vary in at least one of thickness, color, hue, and reflectivity.

8. The method of claim 6, wherein the one or more lines includes black and/or gray lines.

9. The method of claim 1, wherein the one or more static control markings comprises one or more colors.

10. The method of claim 1, wherein the scan surface further comprises a test placement guide proximate the one or more static control markings, wherein the test placement guide is configured to guide placement of the diagnostic test.

11. The method of claim 10, wherein the image region further includes the test placement guide.

12. The method of claim 1, wherein assessing the adequacy of the at least one of lighting, orientation, and focus conditions comprises detecting one or more of a lighting level, a presence of shadows or glare, a misalignment of the scan surface relative to the at least one image sensor, an image blur level, and a noise level of the image.

13. The method of claim 1, wherein the one or more static control markings are printed on the scan surface.

14. The method of claim 1, wherein the one or more static control markings comprise a set of lines varying in thickness or intensity.

15. The method of claim 14, wherein at least one line of the set of lines has a thickness or intensity corresponding to an expected thickness or intensity of a control line or a test line of the diagnostic test.

16. The method of claim 14, wherein the diagnostic test comprises a lateral flow assay, and wherein assessing the adequacy of at least one of the lighting, orientation, and focus conditions comprises determining, based on detection of at least some of the set of lines, that the at least one of the lighting, orientation, and focus conditions are adequate for detection of the test line and the control line on the lateral flow assay following application of a sample to the lateral flow assay.

17. The method of claim 1, wherein the one or more static control markings comprise a plurality of geometric shapes.

18. The method of claim 1, wherein the plurality of image region markers comprises at least three image region markers defining a rectangular boundary of the image region.

19. The method of claim 1, wherein the one or more processors exclude any image pixels outside the image region when assessing the adequacy of at least one of lighting, orientation, and focus conditions associated with the image.

20. The method of claim 1, wherein the one or more processors determine an expected location for the one or more static control markings within the image based on detecting the plurality of image region markers.

21. The method of claim 1, wherein each metric in the 1D array of metrics comprises a mean or a median of the pixel values of the individual one of the multiple linear series of image pixels.

22. The method of claim 1, wherein one or more static control markings comprise a plurality of static control markings, and wherein verifying detection of the one or more static control markings comprises comparing a count of the identified one or more peaks in the 1D array of metrics to a threshold number.

\* \* \* \* \*